United States Patent
Geng

(10) Patent No.: US 7,524,490 B2
(45) Date of Patent: Apr. 28, 2009

(54) CLUSTERIN-MEDIATED INHIBITION OF APOPTOSIS VIA STROMAL BONE MARROW CELL DELIVERY TO A CARDIAC SITE

(75) Inventor: Yong-Jian Geng, Pearland, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/270,432

(22) Filed: Nov. 9, 2005

(65) Prior Publication Data

US 2006/0099194 A1    May 11, 2006

Related U.S. Application Data

(60) Provisional application No. 60/626,820, filed on Nov. 10, 2004.

(51) Int. Cl.
*A01K 67/027* (2006.01)
*A61K 48/00* (2006.01)
*A61K 38/17* (2006.01)

(52) U.S. Cl. .......................... 424/93.1; 514/44; 514/12; 800/18

(58) Field of Classification Search ................ None
See application file for complete search history.

(56) References Cited

U.S. PATENT DOCUMENTS 6,607,720 B1    8/2003    Xiao et al.
6,805,860 B1    10/2004   Alt

OTHER PUBLICATIONS

You, KH et al. Z Naturforsch C 58(1-2):148-151, Jan.-Feb. 2003.*
Gobe, G et al. J Struct Biol 118:63-72, 1997.*
Wang, JS, et al. J THor Cardiovasc Surg 122(4):699-705, 2001.*
Wang, JS et al. J Thor Cardiovasc Surg 120(5):999-1006, 2000.*
Krijnen, PAJ et al. Am J Heart Circ Physiol 289:2193-2202, 2005.*
Wehrli, P et al. Nature Med 7(9):977-979, 2001.*
Tomasoni, S and A Benigni. Current Gene Therapy 4(1):115-122, 2004.*
Yang, X Radiology 228:36-49, 2003.*
Gautam, A et al. Am J Respir Med 1(1):35-46, 2002.*
Ando et al Tohoku J Exp Med 214:159-163, 2008.*
J.S. Odorico, et al., "Multilineage Differentiation from Human Embryonic Stem Cell Lines," Stem Cells 2001; 19:193-204.
M.F. Pittenger, et al., "Multilineage Potential of Adult Human Mesenchymal Stem Cells," Science vol. 284: 143-147 (Apr. 2, 1999).
S. Ramakrishnan, et al., "Stem Cells and Myocardial Regeneration," Indian Heart Journal vol. 55, No. 2 (Mar.-Apr. 2003).
M.C. Rechsteiner, "Ubiquitin-Mediated Proteolysis: An Ideal Pathway for Systems Biology Analysis," Adv. Exp. Med. Biol. 2004; 547: 49-59 (Abstract).
L.A. Passmore, et al., "Getting into Position: The Catalytic Mechanisms of Protein Ubiquitylation," Biochem. J. (2004) 379, 513-525.
M.H. Glickman, "Getting in and out of the Proteasome," Cell & Developmental Biology, vol. 11, 2000: 149-158.
L. Hicke, "Regulation of Membrane Protein Transport by Ubiquitin and Ubiquitin-Binding Proteins," Annu. Rev. Cell Dev. Biol. 2003, 19:141-72.
P. Gagneux, et al., "Evolutionary Considerations in Relating Oligosaccharide Diversity to Biological Function," Glycobiology vol. 9, No. 8: 747-755 (1999).
A. Varki, "'Unusual' Modifications and Variations of Vertebrate Oligosaccharides: Are we Missing the Flowers for the Trees?," Glycobiology vol. 6 No. 7: 707-710 (1996).
A.F.L.Huristone, et al., "The Wnt/β-Catenin Pathway Regulates Cardiac Valve Formation," Nature vol. 425: 633-637 (Oct. 9, 2003).
T. Nakamura, et al., "Wnt- and β-Catenin -Dependent Pathway for Mammalian Cardiac Myogenesis," PNAS vol. 100, No. 10: 5834-5839 (May 13, 2003).
C. Kioussi, et al., "Identification of a Wnt/DvI/β-Catenin—Pitx2 Pathway Mediating Cell-Type-Specific Proliferation During Development," Cell, vol. 111: 673-685 (Nov. 27, 2002).

(Continued)

*Primary Examiner*—Deborah Crouch
*Assistant Examiner*—Marcia S Noble
(74) *Attorney, Agent, or Firm*—Conley Rose, P.C.

(57) ABSTRACT

Methods and compositions are disclosed for inhibiting, deterring or preventing apoptosis of cardiac myocytes, transplanted stem cells, vascular stem cells, and vascular smooth muscle cells by means of expressing or synthesizing clusterin. Also disclosed are methods and compositions for producing recombinant clusterin, or its biologically active peptides, and for induction of clusterin-associated lipoproteins or enzymes for deterring or preventing inflammatory injury and apoptosis induced by oxLDL, oxysterols, cytokines, and Fas Ligand. Also disclosed is an induction method and composition for enhancing expression of ALDH and ALDH-associated enzymes or co-factors to prevent cytotoxicity or detoxification. Therapeutic methods providing new expression or overexpression of clusterin in vascular or cardiac tissue are expected to inhibit the formation of atherosclerotic lesions, stabilize existing atherosclerotic plaques, and repair failing or damaged cardiac tissue.

19 Claims, 7 Drawing Sheets
(1 of 7 Drawing Sheet(s) Filed in Color)

OTHER PUBLICATIONS

S.H. Baek, et al., "Regulated Subset of $G_1$ Growth-Control Genes in Response to Depression by the Wnt Pathway," PNAS, vol. 100, No. 6: 3245-3250 (Mar. 18, 2003).

P. Zhang, et al., "Cooperation between the *Cdk* Inhibitors $p27^{KIP1}$ and $p57^{KIP2}$ in the Control of Tissue Growth and Development," Genes & Development 12:3162-3167 (1998).

M.A. Dyer, et al., "$p27^{Kip1}$ and $p57^{Kip2}$ Regulate Proliferation in Distinct Retinal Progenitor Cell Populations," The Journal of Neuroscience, 21(12): 4259-4271 (Jun. 15, 2001).

M.H. Lee, et al., "Cloning of $p57^{KIP2}$, a Cyclin-Dependent Kinase Inhibitor With Unique Domain Structure and Tissue Distribution," Genes Dev. Mar. 15, 1995; 9(6):639-49 (Abstract).

E.G. Reynaud, et al., "Stabilization of MyoD by Direct Binding to $p57^{Kip2}$," The Journal of Biological Chemistry, vol. 275, No. 25: 18767-18776 (Jun. 23, 2000).

E.G. Reynaud, et al., "$p57^{Kip2}$ Stabilizes the MyoD Protein by Inhibiting Cyclin E-Cdk2 Kinase Activity in Growing Myoblasts," Molecular and Cellular Biology, vol. 19, No. 11: 7621-7629 (Nov. 1999).

V. Grandjean, et al., "Increased IGF-II Protein Affects $p57^{Kip2}$ Expression in vivo and in vitro: Implications for Becwith-Wiedemann Syndrome," PNAS, vol. 97, No. 10:5279-5284 (May 9, 2000).

A.E. Manzi, "Exploring the Glycan Repertoire of Genetically Modified Mice by Isolation and Profiling of the Major Glycan Classes and Nano-NMR Analysis of Glycan Mixtures," Glycobiology, vol. 10, No. 7: 669-689 (2000).

A. Varki, "Factors Controlling the Glycosylation Potential of the Golgi Apparatus," Cell Biology, vol. 8: 34-40 (Jan. 1998).

B.D. Shur, et al., "Cell Surface Galactosyltransferase: Current Issues," Glycoconjugate Journal 15: 537-548 (1998).

R.N. Russo, et al., "Bovine β1-4-Galactosyltransferase: Two Sets of mRNA Transcripts Encode Two Forms of the Protein with Different Amino-Terminal Domains," The Journal of Biological Chemistry, vol. 265, No. 6:3324-3331 (Feb. 25, 1990).

R.N. Russo, et al., "β1, 4-Galactosyltransferase: A Short $NH_2$—Terminal Fragment that Includes the Cytoplasmic and Transmembrane Domain is Sufficient for Golgi Retention," The Journal of Biological Chemistry, vol. 267, No. 13: 9241-9247 (May 5, 1992).

I. Marenholz, et al., "Genetic Analysis of the Epidermal Differentiation Complex (EDC) on Human Chromosome 1q21: Chromosomal Orientation, New Markers, and a 6-Mb YAC Contig," Genomics 37: 295-302 (1996).

B. Causier, "Studying the Interactome with the Yeast Two-Hybrid System and Mass Spectrometry," Mass Spectrometry Reviews, 23: 350-367 (2004).

S. Thaminy, et al., "The Split-Ubiquitin Membrane-Based Yeast Two-Hybrid System," Methods Mol. Biol. 261: 297-312 (2004) (Abstract).

T.T.M. Nguyen, et al., "Expressing Murine β1, 4-Galactosyltransferase in HeLa Cells Produces a Cell Surface Galactosyltransferase-Dependent Phenotype," The Journal of Biological Chemistry, vol. 269, No. 45, 28000-28009 (Nov. 11, 1994).

M.W. Tengowski, et al., "Subcellular Localization of β1, 4-Galactosyltransferase on Bull Sperm and its Function During Sperm-Egg Interactions," Molecular Reproduction and Dev. 58:236-244 (2001).

B. Nixon, et al., "Galacatosyltransferase Function During Mammalian Fertilization," Cells Tissues Organs, 168:46-57 (2001).

I. Marenholz, et al., "Identification of Human Epidermal Differentiation Complex (EDC)-Encoded Genes by Substractive Hybridization of Entire YACs to a Gridded Keratinocyte cDNA Library," Genome Research, 11:341-355 (2001).

K. Hiromura, et al., "Podocyte Expression of the CDK-Inhibitor p57 During Development and Disease," Kidney International, vol. 60:2235-2246 (2001).

J.S. Lebkowski, et al., "Human Embryonic Stem Cells: Culture, Differentiation, and Genetic Modification for Regenerative Medicine Applications," (2001) The Cancer Journal 7, Suppl. 2, Nov./Dec. 2001; 583-593.

C. Rodeheffer, et al., "Targeted Mutations in β1, 4-Galactosyltransferase I Reveal its Multiple Cellular Functions," Biochimica et Biophysica Acta 1573: 258-270 (2002).

E.M. Bayna, et al., "Temporally Specific Involvement of Cell Surface Beta-I, 4 Galactosyltransferase During Mouse Embryo Compaction," Cell. 8; 53 (1): 145-57 (Apr. 8, 1988) (Abstract).

H.J. Harhaway, et al., "Mutational Analysis of the Cytoplasmic Domain of β1, 4-Galactosyltransferase I: Influence of Phosphorylation on Cell Surface Expression," Journal of Cell Science 116: 4319-4330 (2003).

H.J. Hathaway, et al., "Mammary Gland Morphogenesis is Inhibited in Transgenic Mice that Overexpress Cell Surface β1, 4-Galactosyltransferase," Development 122:2859-2872 (1996).

P. Sutovsky, et al., "Accumulation of the Proteolytic Marker Peptide Ubiquitin in the Trophoblast of Mammalian Blastocysts," Cloning and Stem Cells, vol. 3, No. 3 (2001).

E. Pringa, et al., "Disruption of the Gene Encoding the Ubiquitin-Conjugation Enzyme UbcM4 has No Effect on Proliferation and In Vitro Differentiation of Mouse Embryonic Stem Cells," Biochimica et Biophysica Acta 1494: 75-82 (2000).

L. Hicke, "Gettin Down with Ubiquitin: Turning Off Cell-Surface Receptors, Transporters and Channels," Cell Biology, vol. 9 (Mar. 1999) 107-112.

D.A. Hinton, et al., "Altering the Expression of Cell Surface β1, 4-Galactosyltransferase Modulates Cell Growth," Experimental Cell Research 219:640-649 (1995).

T. Kamura, et al., "Rbx1, A Component of the VHL Tumor Suppressor Complex and SCF Ubiquitin Ligase," Science Vo. 284 (Apr. 23, 1999) 657-661.

D. Skowyra, et al., "Reconstitution of $G_1$ Cyclin Ubiquintination with Complexes Containig $SCF^{Grr1}$ and Rbx1," Science, vol. 284 (Apr. 23, 1999) 662-665.

M.J. Wassler, et al., "Clustering of Cell Surface β1, 4-Galactosyltransferase I Induces Transient Tyrosine Phosphorylation of Focal Adhesion Kinase and Loss of Stress Fibers," Journal of Cell Science, 113: 237-245 (2000).

M.J. Wassler, et al., "Functional Interation Between the SSeCKS Scaffolding Protein and the Cytoplasmic Domain of β1, 4-Galactosyltransferase," Journal of Cell Science, 114:2291-2300 (2001).

Q. Lu, et al., "Targeted Mutation in β1, 4-Galactosyltransferase Leads to Pituitary Insufficiency and Neonatal Lethality," Developmental Biology, 181:257-267 (1997).

A.W. Koch, et al., "Structure-Based Models of Cadherin-Mediated Cell Adhesion: The Evolution Continues," Cell. Mol. Life Sci. 61: 1884-1895 (2004).

J.M. Gooding, et al., "The Cadherin-Catenin Complex as a Focal Point of Cell Adhesion and Signalling: New Insights from Three-Dimensional Structures," BioEssays 26:497-511 (2001).

C. Ham, et al., "ADAM15 is an Adherens Junction Molecule Whose Surface Expression Can be Driven by VE-Cadherin," Experimental Cell Research 279: 239-247 (2002).

U. Steinhusen, et al., "Cleavage and Shedding of E-Cadherin After Induction of Apoptosis," The Journal of Biological Chemistry, vol. 276, No. 7:4972-4980 (Feb. 16, 2001).

L. Larue, et al., "E-Cadherin Null Mutant Embryos Fail to Form a Trophectoderm Epithelium," Proc. Natl. Acad. Sci. USA. vol. 91: 8263-8267 (Aug. 1994).

L. Larue, et al., "A Role For Cadherins in Tissue Formation," Development 122: 3185-3194 (1996).

P. Rosenberg, et al., "A Potential Role of R-Cadherin in Striated Muscle Formation," Developmental Biology 187:55-70 (1997).

U. Dahl, et al., "Genetic Dissection of Cadherin Function During Nephrogenesis," Molecular and Cellular Biology, vol. 22, No. 5: 1474-1487 (Mar. 2002).

H. Haegel, et al., "Lack of β-Catenin Affects Mouse Development at Gastrulation," Development 121: 3259-3537 (1995).

A. Novak, et al., "Signaling Through β-Catenin and Lef/Tef," Cell. Mol, Life Sci 56:523-537 (1999).

Koch-Brandt, C. et al., "Clusterin: A Role in Cell Survival in the Face of Apoptosis?", Prog Mol Subcell Biol., 1996, 16: 130-49; Abstract found at: http://www.ncbi.nlm.nih.gov/sites/entrez.

Krijnen, P.A. et al., "Clusterin: A Protective Mediator for Ischemic Cardiomyocytes?", Am. J. Physiol Heart Circ. Physiol, 289: H2193-H2202, 2005.

Mackness, B. et al., "Increased Immunolocalization of Paraoxonase, Clusterin, and Apolipoprotein A-I in the Human Artery Wall with the Progression of Atherosclerosis", Thromb Vasc Biol. Jul. 1997 17(7):1233-8. Abstract found at: http://www.ncbi.nlm.nih.gov/sites/entrez?Db=pubmed&Cmd=ShowDetailView&TermToSearch=9261251&ordinalpos=2&itool=EntrezSystem2.PEntrez.Pubmed.Pubmed_ResultsPanel.Pumbed_RVDocSum.

* cited by examiner

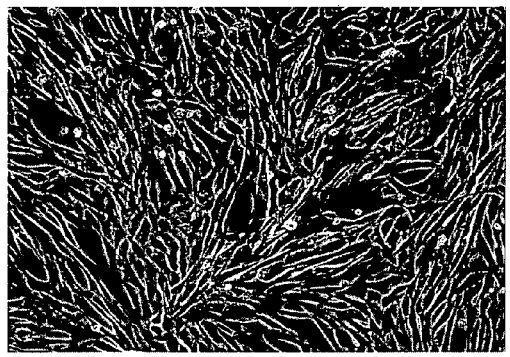 
FIG. 6A  FIG. 6B
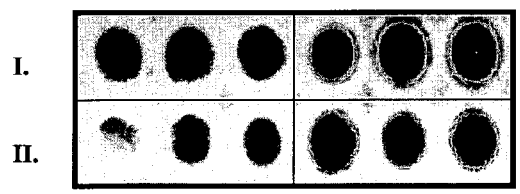
FIG. 10

CLUSTERIN-MEDIATED INHIBITION OF APOPTOSIS VIA STROMAL BONE MARROW CELL DELIVERY TO A CARDIAC SITE

CROSS-REFERENCE TO RELATED APPLICATION

This application claims the benefit under 35 U.S.C. § 119 (e) of U.S. Provisional Patent Application No. 60/626,820 filed Nov. 10, 2004, the disclosure of which is hereby incorporated herein by reference

BACKGROUND OF THE INVENTION

1. Field of the Invention

The present invention generally relates cellular therapy and tissue engineering for treating atherosclerosis and heart failure, and more particularly to the synthesis and expression of clusterin (apolipoprotein-J) and its use in cellular therapy and tissue engineering, especially for protecting embryonic and adult stem cells against inflammatory injury and apoptosis.

2. Description of Related Art

Cellular therapy with multipotent stem cells for treatment of myocardial infarction and ischemic heart failure. During the development of ischemic heart failure caused by disruption of coronary circulation, progressive loss of functional myocytes occurs in the myocardium. Since adult mature myocytes do not proliferate, the damaged myocardium is replaced by connective tissue composed of non-cardiomyocytic cells and extracellular matrix and a scar surrounded by hypertrophied myocytes. By contrast, fetal cardiac myoblasts or stem cells can proliferate and differentiate into adult myocytes. Fetal myogenic stem cell proliferation remains active until the second week after birth. Recent studies have suggested that implantation of fetal cardiac or skeletal myoblasts[1-4] may help heal an experimentally infarcted heart. These studies show that when implanted in the infarcted adult heart, embryonic myoblasts may survive, proliferate, and communicate with host cells in the myocardium. Using a swine model, van Meter, et al.[6,7] reported that transplanted myoblasts formed close associations with host myocytes that resembled nascent intercalated disks on electron microscopy. These cells also contained myofibrils and other cell architecture resembling the transplanted cell lines, and they may exert an angiogenic influence resulting in the proliferation of the surrounding microvasculature.

In spite of the rapid progress in the studies of myocyte implantation, there is little information concerning the differentiation of the implanted fetal myocytes in the heart. The cell lineages in the heart, including cardiac myocytes, vascular cells and interstitial cells, are derived from embryonic stem cells. In addition to highly mature cardiac myocytes, some embryonic myoblasts, in particular those located in subepicardium, may differentiate into coronary arterial cells. It is now accepted that coronary arteries form originally in the subepicardial area and subsequently grow into the aorta. During embryonic development, the first signs of coronary vessel formation appear as blood island-like structures or endothelial tubes in the subepicardium.

In addition to fetal or embryonic tissues, adult or newborne tissues may contain certain numbers of stem cells that differentiate into mature, functional cells in different organs. One of the major resources for adult stem cells is the bone marrow. Many studies recently have shown that stem cells from both human and animal bone marrows can differentiate into myocyte-like cells.[1,4] Transplantation of bone marrow stem cells into the heart with experimental infarction leads to development of neomyocardial and neovascular tissues as well as improvement of heart function.

U.S. Pat. No. 6,805,860 (Alt) describes a process for repairing tissue of a patient's heart, which comprises delivering stem cells, preferably autologous stem cells, to the site of tissue to be repaired. The stem cells are injected through a catheter to invade the failing tissue at the site, while local forces at the site are quelled from disrupting migration of the stem cells into the failing tissue.

U.S. Pat. No. 6,607,720 (Xiao, et al.) describes a therapeutic method for improving cardiac function after myocardial infarction using genetically altered mammalian embryonic stem cells. Exemplary cDNAs said to be useful for transfection are VEGF (vascular endothelial growth factor); $FGF_{1,2}$ (fibroblast growth factor 1 and 2); TGF-$\alpha$ & $\beta_{1-5}$ (transforming growth factor $\alpha$ & $\beta_{1-5}$; IGF-1 & -2 (insulin-like growth factor 1 & 2); SERCA I & II (sarco/endoplasmic reticulum $Ca^{2+}$ ATPase I & II); $\beta_2$ (beta adrenergic receptor II); Gs-protein (stimulatory guanosine-binding protein); $Ca.^{2+}$ channel (calcium channel); and telomerase.

Because of the limited supply of autologous stem cells, most studies use allogenic stem cells for transplantation. In general, stem cells are weak antigens that evoke little immune reaction. However, allogenic stem cells are transplanted frequently into the heart with infarction where they confront a very harsh environment. Local inflammation, oxidative stress and cytotoxic radicals and proteins may cause death of the transplanted cells primarily via an apoptotic mechanism. Even in the weak immune reaction to stem cells, long-term exposure to activate immune cells and their cytokine products may also trigger cell death by apoptosis. Apoptosis is a form of genetically programmed cell death that represents a major mechanism by which tissue removes unwanted, aged or damaged cells under both physiological and pathological conditions. Morphologically, apoptosis is characterized by chromatin compaction and margination, by nuclear condensation and fragmentation, and by cell shrinkage and blebbing.

Apoptosis may occur abnormally leading to accelerated cardiac cell death during heart failure, as demonstrated in animal models.[8] During the development of atherosclerosis, accumulating free cholesterol undergoes oxidation, producing oxysterols with higher cytotoxicity to vascular cells. In vitro studies have shown that some oxysterols such as 7-ketocholesterol exerts potent apoptotic effects on stem cells. Oxysterols are considered to be major cytotoxic components of oxidized low density lipoprotein (oxLDL). It has been shown that CD95 is present in human plaque, and it was proposed that activation of CD95 may mediate apoptosis of stem cells in the presence of IFN$\gamma$ and TNF$\alpha$. (Geng et al, *Arterioscler Thromb Vasc Biol.* (1997) 17:2200-8). The role for apoptosis in the development of neocardiovascular tissues remains unclear, however.

Clusterin (Apolipoprotein-J)[12] is a sulfated, heterodimeric glycoprotein containing two 40 kDa chains joined by a unique five disulfide bond motif, as schematically illustrated in FIG. 1. Encoded on a 2-kb mRNA, clusterin is transcribed from a single copy gene located on mouse chromosome 14.[13] It contains several domains, such as amphipathic helix, heparin-binding domain, and lipid-binding domain. This protein was initially identified from ram rete testes fluid and named for its ability to elicit clustering of Sertoli cells supporting sperm maturation and development (NCBI/GenBank Accession No._NM_203339, NM_001831) Thereafter, species homologues have been isolated and cloned by a number of groups working in widely divergent areas, resulting in a number of synonyms including testosterone repressed prostate message-2 (TRPM-2), sulfated glycoprotein-2 (SGP-2), apolipoprotein-J (clusterin), SP-40, 40, complement cytolysis inhibitor (CLI), and dimeric acidic glycoprotein (DAG), gp 80, NA1/NA2, glycoprotein III, etc. Clusterin is constitutively expressed by various tissues and cells, in virtually all body fluids, and on the surface of cells lining body cavities. It circulates in blood with the high density lipoprotein (HDL) fractions, and thus considered as a component of HDL in which clusterin is associated with apolipoprotein-AI and paraoxonase (NCBI Accession No. NM_000446). The latter protein is one of the key enzymes with antioxidant property. Clusterin and its associated proteins are present at high levels in the lesions of patients with atherosclerosis.[25] Clusterin is translated as a typical hydrophobic signal peptide with 21 amino acids in length.[14] The biological functions of clusterin have not been completely known. Reported functions of clusterin include apoptosis regulation, complement defense, lipid recycling, membrane protection, and maintenance of cell-cell or cell-substratum contacts. It can effectively bind to lipids including both cholesterol and oxysterols, and has been shown to promote efflux of cholesterol and oxysterols from lipid-laden foam cells. This protein can also inhibit complement-mediated cell death, and promote cell aggregation and adhesion. Recently, clusterin has been found to be an anti-apoptotic protein. It has been reported that clusterin expression is induced and confers resistance to apoptotic cell death induced by heat shock and oxidative stress. High levels of clusterin have been shown in tissues with apoptosis. However, careful analysis of the producing cells revealed that clusterin expression is restricted to the vital cells adjacent to dead cells, suggesting that this molecule may act as a cell survival factor, which protects bystander cells. Recent studies have shown that clusterin is an anti-apoptotic protein.[15]

Developmental regulation of clusterin expression has been reported in many tissues including the heart, kidney, lung, and brain.[16,17] In the heart, clusterin is found in both the atria and ventricles of the fetal mouse heart, but in the adult heart, only the atria show positive stains for clusterin.[13] However, marked induction of clusterin can be detectable in the heart with acute infarction[18], in particular the peri-infarct zone.[19] Induction of clusterin is also observed in the myocardium with inflammation,[20] suggesting a protective effect of clusterin in the inflammatory myocardium. Clusterin-deficient mice appear to be more sensitive to develop myocarditis than age-and sex-matched wild type controls. In the kidney, clusterin is expressed in the ureteric bud but not in surrounding mesenchyme.[21] When the mesenchyme is induced to differentiate into renal epithelium, clusterin expression takes place and continues in developing tubules. In newborn mice, almost all the tubules express clusterin, but adult tubules rarely express clusterin. Similar to the time course in the heart and kidney, the developing fetal but not adult lung contains clusterin.

The temporal expression of clusterin during ontogeny and tissue injury implies a role for clusterin in organogenesis and tissue remodeling, perhaps through regulation of stem cell proliferation, differentiation and apoptosis, and interactions with other cellular components or extracellular matrix.[16] Little and Mirkes[22] recently investigated the relationship between clusterin expression, normal programmed cell death (PCD) in the developing rat limb bud, and abnormal cell death induced by hyperthermia in day 11 rat embryos. They observed that clusterin mRNA and protein were expressed at high levels in the heart, a tissue that is completely resistant to the cytotoxic effects of hyperthermia. Similar finding occurs in the developing brain. Clusterin expression occurs in the earliest neurons of the cortical plate on embryonic day (E) 12, and can continue to increase in an age-dependent manner, with the greatest intensity of expression being found in the postnatal mature brain.[23] Clusterin is also frequently found in neuron degenerative disorders, such as Alzheimer's disease.[24]

In order to better implement the full potential of stem cell transplantation for treatment of atherosclerosis, myocardial infarction and heart failure, new ways are needed to promote or enhance the success of cellular therapy, including improving the survival of transplanted cells.

SUMMARY OF THE INVENTION

Protection of stem cells from inflammatory injury and apoptosis as an aid to successful cellular therapy and tissue engineering is described. This will have applicability for treating atherosclerosis and heart failure, in particular. It is demonstrated herein that cardiac and vascular myocytes are derived from common progenitors in the heart, and that when implanted into an injured adult heart, the progenitor cells differentiate into both cardiac and vascular cells, and promote healing of the damaged myocardium. The synthesis and expression of clusterin (apolipoprotein-J) and its use in cellular therapy and tissue engineering are described herein, with emphasis on protecting embryonic and adult stem cells against inflammatory injury and apoptosis.

In accordance with certain embodiments of the invention, a method of inhibiting apoptosis in mammalian cells is provided. For the purposes of this disclosure, the terms "inhibiting" and "inhibition" have their usual meanings in the art and include deterring, preventing, deterrence and prevention of apoptosis or apoptotic cell death. The method comprises contacting the cells and/or the surrounding microenvironment (e.g., in vitro cell culture, adjacent or "bystander" cells in vivo) with an amount of clusterin effective to inhibit apoptosis or programmed cell death. The cell-secreted amount of clusterin is effective to inhibit or prevent apoptosis or programmed cell death in distant tissues. In certain embodiments, transfection of a nucleotide encoding clusterin in cells of a mammalian tissue causes sufficient expression of clusterin, effective to inhibit apoptotic cell death in the tissue. In certain embodiments, the step of causing the expression of an amount of a nucleotide encoding clusterin includes transfecting cells of the tissue with a DNA sequence encoding the entire clusterin peptide sequence, in its entirety or in part (i.e., a biologically active portion of the clusterin sequence), operably linked to a promoter and capable of being expressed in the cells to provide an amount of clusterin sufficient to inhibit apoptotic cell death in transfected and/or non-transfected cells of the tissue. For the purposes of this disclosure, the term "biologically active portion" refers to an entire native clusterin molecule, or to a portion of such molecule, that has the ability to mediate, to at least some extent, the same apoptosis-inhibitory effect of a native clusterin molecule. In some embodiments, the method includes transfecting one or more cell by means of a vector, such as plasmids, phages, viruses (e.g., adenovirus or an adenoassociated virus).

In certain other embodiments the method comprises causing the expression of clusterin in a tissue by first, carrying out the in vitro synthesis of clusterin using recombinant DNA technology, then bioengineering stem cells with the gene coding for clusterin, and determining the presence and/or amount of clusterin. In some embodiments, clusterin-associated or regulated proteins are also determined. Finally, the bioengineered cells, and/or the clusterin product, are delivered into a tissue suffering from, or at risk of being subjected to, physical and/or chemical injury. In some embodiments the tissue is vascular tissue or cardiac tissue. In certain embodiments, the vascular or cardiac tissue is affected with atherosclerosis or heart failure. In other embodiments, the vascular or cardiac tissue is not affected with atherosclerosis or heart failure. In some embodiments, the cells are one or more of the cell types: stem cells, vascular stem cells, cardiac myocytes and/or vascular cells (e.g., vascular smooth muscle cells). In some embodiments, the stem cells are autologous or allogenic transplanted stem cells (e.g, bone marrow derived). In preferred embodiments, the stem cells are uncommitted and are capable of differentiating into cardiac or vascular cells, prior to implantation.

In certain embodiments of an above-described method of inhibiting apoptosis in mammalian cells, the step of causing the expression of an amount of nucleotide encoding clusterin includes transplanting genetically modified mammalian stem cells into a tissue, wherein the genetic modification comprises, a DNA sequence encoding clusterin, or a biologically active portion thereof, integrated into the genome of the stem cell and operably linked to a promoter. As a result, the DNA encoding clusterin is able to be expressed in cells of the tissue to provide an amount of clusterin sufficient to inhibit apoptotic cell death in cells of the tissue.

In some embodiments, certain of the above-described methods provide clusterin mediated enhancement or promotion of expression and activation of clusterin-associated or clusterin-regulated proteins or enzymes, including, but is not limited to, aldehyde dehydrogenases. In some embodiments apoptosis is induced by at least one agent selected from the group consisting of oxysterols, oxLDL, cytokines and Fas Ligand.

In accordance with certain embodiments of the present invention, a method of treating or preventing atherosclerosis, or a complication thereof in a mammal, is provided. For the purposes of this disclosure, the term "preventing" atherosclerosis has its usual meaning in the art and includes "deterring" and "reducing the risk of" atherosclerosis. This method comprises carrying out an above-described method wherein the tissue is a cardiac or vascular region comprising an atherosclerotic lesion, or an area that is at risk of forming an atherosclerotic lesion, and wherein the contacting of cells in the tissue with clusterin deters or prevents apoptotic cell death sufficiently to prevent, or reduce the risk of, formation of an atherosclerotic lesion. In some embodiments, the contacting of cells in the tissue with clusterin deters or prevents apoptotic cell death sufficiently to prevent, or reduce the risk of, rupture of an atherosclerotic lesion. In certain embodiments, the step of causing the expression of an amount of clusterin in the tissue comprises transfecting cells in the tissue with a nucleotide sequence encoding clusterin, or a biologically active portion thereof, capable of being expressed in the cells. In certain embodiments, the cells are chosen from the group consisting of vascular cells, cardiac myocytes and transplanted stem cells. In some embodiments, the stem cells are bone marrow derived stem cells or vascular stem cells.

In certain embodiments, the atherosclerotic lesion comprises an aneurism in a vessel. In certain embodiments, the atherosclerotic lesion comprises an unstable plaque caused by hyperlipidemia and the amount of clusterin contacting a treatment site is effective to stabilize the plaque (i.e., reduce the risk of rupture of the plaque, thrombus formation, or other complication).

In certain of the above-described methods, the amount of clusterin is effective to deter or prevent apoptosis and/or protect against inflammatory injury, induced by at least one agent chosen from the group consisting of: oxidized low density lipoprotein (oxLDL), oxysterols, cytokines and Fas ligand.

Another embodiment of the present invention provides a method of treating heart failure in a mammal, which comprises transplanting into the heart of the mammal an amount of transgenically modified cardiac myocytes over-expressing sufficient clusterin, or transgenically modified stem cells over-expressing sufficient clusterin, to improve heart function and protect the transgenically modified myocytes and/or stem cells and their adjacent cells from inflammatory injury.

In accordance with still another embodiment of the present invention, a transgenic mouse is provided. This transgenic mouse comprises a transgenic DNA sequence encoding clusterin, or a biologically active portion thereof, stably integrated into the genome of the mouse, and operably linked to a promoter. For the purposes of this disclosure, the term "stably integrated" means that the exogenous clusterin gene with its vector genes, in part or whole, incorporate into genomic DNA and can be passed into daughter cells for at least multiple generations, preferably for unlimited generations. Accordingly, the DNA sequence, or portion thereof, is expressed in the mouse, and, as a result of the expression, the transgenic mouse has an increased level of serum clusterin relative to the serum clusterin level in a mouse that does not express the same transgenic DNA sequence, or portion thereof. In certain embodiments, the serum from the transgenic mouse has increased oxysterol-binding activity relative to the oxysterol-binding activity of serum from a mouse that does not express the transgenic nucleotide sequence, or portion thereof. In certain embodiments, the vascular cells of the transgenic mouse have reduced risk of atherosclerotic lesion formation relative to that of a mouse that does not express the transgenic nucleotide sequence, or portion thereof.

Still other embodiments of the present invention provide a method of producing or synthesizing full-length or part of clusterin for inducing or causing the expression of at least one gene encoding a protein or enzyme for detoxification chosen from the groups consisting of aldehyde dehydrogenases, apolipoprotein-AI and paraoxonase. In certain embodiments, production or expression of clusterin, or a biologically-active portion thereof, occurs naturally or by recombinant technique or cDNA transduction in at least one vector chosen from the group consisting of plasmids, yeasts and viruses. In certain embodiments, the native or recombinant clusterin, or portion thereof, occurs in one or more type of mammalian cell, preferably cardiac and vascular cells. In certain embodiments, the aldehyde dehydrogenase enzyme that is induced by clusterin acts as a detoxification agent for oxidized lipoproteins and oxysterols, and thus has anti-atherosclerosis activity. In certain embodiments, the aldehyde dehydrogenase is a peptide encoded by a nucleotide expressed in one or more type of mammalian cell, including, but not limited to, vascular cells, cardiac cells, and undifferentiated stem cells. In certain embodiments, the aldehyde dehydrogenase enzyme is an isoform, and recombinant clusterin expression and production occurs in one or more mammalian tissue (e.g., heart, blood vessel, liver, kidney and brain) resulting in at least some measure of protection against cytotoxic attack by oxidative stress and/or ischemic injury.

Still another embodiment of the present invention provides a method of administering stem cells with enhanced expression of recombinant clusterin, or that have been treated with clusterin, into a tissue or organ. In some embodiments, the tissue or organ comprises a failing heart or an atherosclerotic blood vessel. In some embodiments, the stem cells are administered by intravenous injection, intra-arterial catheter, or by intramuscular or intratissue injection. In certain embodiments, the stem cells are delivered or injected together with an agent that causes vascular dilation and/or are co-administered with an anti-thrombotic agent. These and other embodiments, features and advantages of the present invention will be recognized by those of skill in the art from the following detailed description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-B are representative images of GFP-transfected fetal cardiac myoblasts, illustrating GFP cDNA transfection leading to expression of the GFP in fetal cardiac myoblasts. FIG. 6A is a phase-contrast image. FIG. 6B is a fluorescent image showing GFP positive cells 48 hours after transfection.

FIG. 7A: clusterin expression in tetracycline-uninduced (lanes 1, 2) and -induced (lanes 3, 4) cells. FIG. 7B: apoptosis in uninduced, clusterin-low cells. FIG. 7C: apoptosis in induced, clusterin-high cells.

FIG. 10 is a group of dot blots shows clusterin binding to free cholesterol and 7-ketocholesterol in clusterin transgenic (TG) and wild type (WT) mice.

DETAILED DESCRIPTION OF THE PREFERRED EMBODIMENTS

For the purposes of this disclosure, the term "clusterin" refers to the apolipoprotein-J originally derived from ram rete testes (NCBI Acc. No. NM_203339, NM_001831), and to homologous proteins derived from other mammalian species, including human, whether denominated as clusterin or not. The sequences of numerous clusterin species are known and have been assigned NCBI accession numbers (NCBI Acc. No. NM_013492, NM_053021, NM_012679).

It is now proposed that clusterin, as a multifunctional protein, may play an important role in regulation of cardiovascular stem cell survival, proliferation and differentiation. The present investigation of the molecular mechanisms underlying the clusterin role in the development of neomyocardium and neovascular tissues in the infarcted hearts transplanted with fetal stem cells is described herein. Information on synthesis and expression of several clusterin associated or regulated proteins or enzymes are also disclosed, which include, but not limited to, caspases, high density lipoproteins, apolipoprotein-A, paraoxonase, and aldehyde dehydrogenase (ALDH). Methods for detecting and preparing clusterin are described herein. Accordingly, the strategic synthesis and expression of clusterin (apolipoprotein-J or apoJ) and its use in cellular therapy and tissue engineering for protecting embryonic and adult stem cells against inflammatory injury and apoptosis are encompassed in the present invention. The application of clusterin in tissue repair and response against lipid cytotoxicity of oxLDL and associated oxysterols, and in preventing atherosclerosis plaques from rupturing or development of complications is also described herein.

General Methods and Materials

Stem cell preparation and culture. The protective effects of clusterin on three types of mouse stem cells were tested. The three cell types are fetal or neonatal cardiac myoblasts, embryonic stem (ES) cells, and bone marrow stromal cells. Fetal or neonatal hearts were collected freshly from C57BL/6J mice and digested with collagenase II/DNase I, and cultured in DMEM serum-free medium supplemented with antibiotics and insulin. Non-myocytic cells were separated by Percoll gradient purification of cardiomyocytes. Since mature myocytes will not be adherent to culture dish and die quickly under the low oxygen condition, adherent, multipotent fetal or neonatal myoblasts were collected by using collagenase digestion after removing non-adherent or dead cells. Mouse ES cell line, D3, obtained from ATCC, has been cultured in the inventors' laboratory, and was used for these studies. Mouse bone marrow stromal cells were isolated by needle inspiration. Stromal cells were separated from blood cells, vascular cells and fibroblasts by use of magnetic beads coated with anti-stromal cell antibodies. Cells were also grown in DMEM medium with 5% fetal bovine serum.

Figure 1:
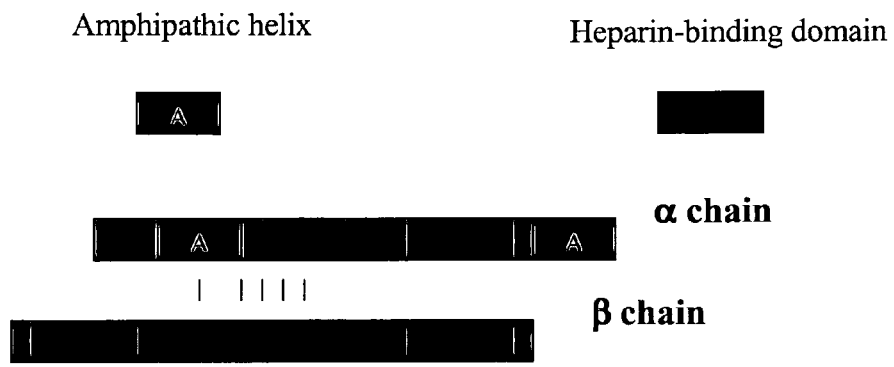
FIG. 1 is a schematic representation of the molecular structure of clusterin.
Figure 2:
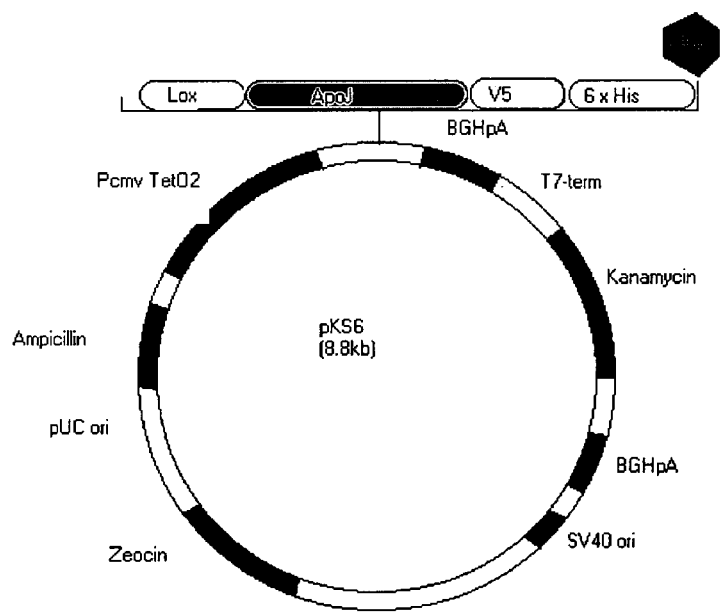
FIG. 2 is a schematic representation of the plasmid pKS56 with a clusterin cDNA-His insert.
Figure 12:
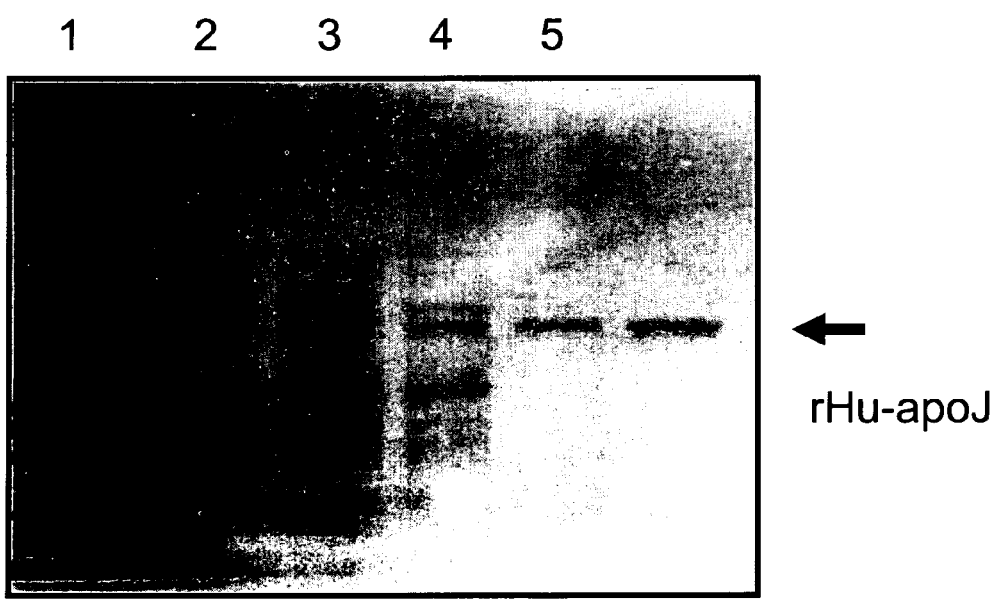
FIG. 12 is a Coomassie blue dye-stained polyacrylamide gel with unpurified (lanes 1-4) and purified (lanes 5-6) recombinant clusterin (apoJ) fractionated by electropherosis.

Preparation of native and recombinant clusterin. To treat stem cells with clusterin, two forms of clusterin were prepared. One is the native clusterin (NCBI ACCESSION No. NM_0134921]. Clusterin was prepared from blood plasma using affinity chromatography with anti-clusterin antibody, In addition, a plasmid was constructed in which mouse or human clusterin cDNA is connected with a His-tag and inserted under a CMV promoter. Schematic presentation of the plasmid pKS56 with a clusterin cDNA-His insert is shown in FIG. 2. pKS56 was constructed by inserting clusterin (clusterin)-His cDNA under the promoter CMV into pGlow-TOPO plasmid (Invitrogen). This promoter also contains a tetracycline-regulatory element. Stable transfection was achieved by using zeocin as a zeocin-resistant gene is also included in the vector. Recombinant clusterin produced by transfected 293 cells was purified by His-tag removing kits. The purity of recombinant clusterin was examined by polyacrylamide gel electrophoresis (FIG. 12).

Treatment of stem cells in culture. An in vitro system was first employed to examine the protective effects of clusterin on stem cells. Stem cells were treated with clusterin at different concentrations in the cultures with or without proinflammatory cytokines or T lymphocytes pre-activated by mitogens. After 2-4 days of stimulation, cell survival and apoptosis were examined using a combination of techniques including flow cytometry, fluorescent microscopy, and radioactive isotope labeling, as described below. Control experiments were set up using other types of proteins, such as bovine albumin.

Detection of apoptotic cells. Determination of apoptosis needs a combination of techniques in morphology and biochemistry. Apoptosis was detected using the following six techniques: 1) Light microscopy; 2) Fluorescent confocal scanning or non-confocal microscopy, 3). In situ labeling of DNA 3' ends (TUNEL technique), 4) Electron microscopy, 5) DNA agarose gel electrophoresis, and 6) Flow cytometry. These techniques are describe more particularly as follows: 1) Light microscopy was applied routinely to analyze morphological changes of vascular cells. 2) Fluorescent confocal scanning or non-confocal microscopy was used to characterize cytoskeletal and nuclear alterations after immunofluorescent staining. DAPI or Hoechst dye was used for nuclear morphology under UV excitation. 3). In situ labeling of DNA 3' ends (TUNEL technique). In principle, the enzyme, terminal deoxynucleotidyl transferase (TdT), which catalyzes a template-independent addition of deoxyribonucleotide to 3'-OH ends of DNA, was used to incorporate digoxigenin-conjugated dUTP to the ends of DNA fragments. The signal of TdT-mediated dUTP nick end labeling (TUNEL) was detected by an anti-digoxigenin antibody conjugated with peroxidase, a reporter enzyme which catalytically generates a brown color product from the chromogenic substrate diaminobenzidine. After TUNEL, counterstaining was performed by immersing the slides in methyl green or by fluorescent staining of nuclei with DAPI (UV) or YOYO-1 (FITC). Alliteratively, to confirm the specificity of the DNA end labeling, a fluorescent method was also used to determine nuclear DNA fragmentation. Fixed cells were incubated with a labeling solution containing biotin-16-dUTP in the presence of TdT (Boehringer Mannheim) for 30 min, washed in PBS, and then probed with fluorescein-isothiocyanate (FITC)-labeled ExtrAvidin (Sigma) in 4× concentrated SSC buffer, 0.1% Triton X-100, and 5% nonfat dry milk. Nuclear counterstaining was performed with propidium iodide, or preferably, with DAPI or Hoechst dye. 4) Electron microscopy. To determine the ultrastructure of cells undergoing apoptosis, transmission electron microscopy was performed. 5) DNA agarose gel electrophoresis. Internucleosomal DNA fragmentation characterizes apoptosis biochemically. To determine whether cells die by apoptosis or necrosis, DNA was isolated from cells using the classic phenol/chloroform extraction method. DNA was precipitated in ethanol, and analyzed for fragmentation by 2% agarose gel electrophoresis with ethidium bromide. 6) Flow cytometry using a state-of-the-art flow cytometer (Beckman-Coulter). In this study, cell proliferation and apoptosis were analyzed by flow cytometry. Cells were labeled with anti-caspase antibodies or anti-Annexin V with propidium iodide nuclear counterstaining.

Transfection with clusterin cDNA. Initially a plasmid was constructed that contains a truncated form of clusterin cDNA with deletion of the sequence responsible for cross-membrane transport. Transfection of human embryonic 293 cell line with this plasmid leads to intracellular overexpression of a non-secreted form of clusterin. The clusterin gene is under control of a CMV promoter with tetracycline-sensitive elements. Transfected cells do not express clusterin until they are exposed to tetracycline. This plasmid will be used to deliver the truncated clusterin gene into stem cells. The cells will be selected using G418 as the plasmid contains a neomycin-resistant gene.

Flow cytometry and immunoblotting. To further determine expression of clusterin, stem cells are treated with tetracycline, and subjected to flow cytometry which quantitatively measures the levels of clusterin as well as apoptosis. Cells are stained with anti-clusterin antibodies conjugated with the fluorochrome FITC or PE and analyzed in a flow cytometer. In some experiments, double staining is performed by using a combination of two or three antibodies to caspases and Fas or CD95. Data is analyzed using a suitably programmed computer. For immunoblotting, total proteins are isolated from treated and untreated cells, and load 30 µg/lane proteins into SDS-PAGE. After electrophoresis, fractions of proteins will be electrotransferred onto a PVDF membrane, and probed with anti-clusterin or other antibodies. The membrane will be developed by using a chemiluminescence kit.

CD95 and CD95L expression and activation. Whether clusterin-transfected or expressing stem cells produce different levels of CD95 or Fas and its ligand from native, untransfected stem cells is determined by flow cytometry and immunoblotting for expression of CD95 and CD95 ligand, as described above. Apoptosis is also analyzed in the clusterin-overexpressing stem cells using the methods described above, including in situ labeling of DNA fragments, DNA agarose electrophoresis and morphometry. In addition, the caspase activation and mitochondrial function are determined as described below.

Mitochondrial transmembrane potential. Decrease in mitochondrial transmembrane potential ($\Delta\psi_m$) is one of the early events of apoptosis. Several types of membrane-permeable lipophilic cationic fluorochromes, such as DiOC6 and rhodamine 123, can serve as probes for analysis of the potential in flow cytometry. When live cells are incubated in their presence, the probe accumulates in mitochondria and the extent of their uptake, measured by the intensity of the cellular fluorescence, is considered to reflect $\Delta\psi_m$. Cells were cultured in DMEM medium with 10% fetal bovine serum and exposed to CD95L in the presence of IFNγ and TNFα. The cells were collected for flow cytometry at 488 nm line of the argon ion laser for blue light, 530 nm for green and 600 nm for red. A combination of Rh 123 and PI labels non-apoptotic cells green, early apoptotic cells dim green, and late apoptotic cells red. The $\Delta\psi_m$ decrease is usually reflected by reduced intensity of the green fluorescence. The data was analyzed in a computer program for quantitation.

Cyt-C release. Cytochrome C (cyt-C) release from mitochondria is a key step for many cell types undergoing apoptosis. Through an adaptor protein, cyt-C can activate caspase-9 and then a DNase, leading to a final episode of apoptosis. To detect cyt-C release from mitochondria, cytosolic proteins were collected for immunoblotting after the oxysterol stimulation. Cellular membrane were permeabilized with digitonin (10 µg/ml), while mitochrondrial membrane remains intact as digitonin has no effect to mitochondria. After permeabilizing cellular membrane, the cells were centrifuged and supernatants were collected for immunoblotting with anti-cyt-C antibody (PharMingen). The cytosolic proteins in the supernatants were tested for protein concentration by using a BCA protein assay kit. 30 µg/lane proteins was loaded into SDS-PAGE gels (10%), and fractionated by electrophoresis. The fractionated proteins were transferred onto PVDF membrane using a semi-dry protein-transferring device (BioRad). After blocking with 4% fat-free milk, the membrane was incubated with rabbit anti-cyt-C, and peroxidase-conjugated second antibody to rabbit IgG was used to detect the antibody.

Detection of clusterin expression at mRNA and protein levels. Two methods were used for determination of clusterin mRNA levels. The first method is Real-time RT-PCR using a quantitative, real-time PCR cycler (Smart Cycler, Cepheid, Suwance, Ga.). The second method is RNase protection assays. Total RNA was isolated from cultured cells or tissues using a RNA isolation kit from Promega. For determination of clusterin protein levels, immunoblotting with anti-clusterin was performed.

Mouse myocardial infarction and stem cell transplantation. In order to examine in vivo functions of clusterin, a mouse infarct model was used. Adult mice (C57BL/6J) at 4-8 months and both sexes were used in the studies. Animals were anesthetized with intramusclar administration of ketamine (20 mg/kg) followed by intraperitoneal injection of pentobarbital. The animals were then intubated, and positive pressure ventilation was maintained with oxygen supply. The heart was exposed through left lateral thoracotomy. Infarcts of the hearts were created by ligation of coronary arteries or by cryoinjury with a metal probe pre-cooled to −190° C. by immersion in liquid nitrogen. Stem cells suspended in PBS or saline with or without clusterin were injected into the hearts with infarcts. Cells were not only injected into infarcted areas, but healthy regions or risk areas were also provided with the stem cells to determine cell survival in different regions of the hearts. Stem cells were labeled with fluorescent dyes such as DAPI or acridine orange. In some cases, GFP cDNA-transfected stem cells were used for transplantation.

Physiological and pathological analysis. The hearts transplanted with stem cells were analyzed for alterations in function and morphology by various techniques in physiology and pathology. Eight weeks after operation, the animals were examined for heart function. Mouse echocardiography and EKG were performed to determine any difference in cardiac performance and electrophysiology. For pathological analysis, the hearts were taken out and fixed in formalin. H&E staining were performed on the sections of the hearts. Since paraffin sections may not be suitable for immunohistochemistry with some antibodies, sections were cut using a cryostat. In some experiments, part of the hearts were collected for proteins and mRNA examination.

Analysis of autoimmune antibodies and T cells against to stem cells. Allogenic stem cells were used for transplantations in this study. Although allogenic stem cells are weak antigens and do not trigger strong immune reaction, chronic immune rejection may occur in certain animals which are prone to autoimmune disorders. Therefore, it was investigated whether anti-stem cell autoantibodies and T cells exist in C57BL/6J mice which receive cell transplantation. The blood from the animals was collected for preparation of immunoglobulin and T cells. A cell lysis assay with the complemental factors was used for determination of the autoantibody activities against the stem cells. Stem cells were labeled with the fluorescent dye DAPI and then incubated with freshly prepared immunoglobulin for 2 hours. The complemental factors C3 and C4 were added into the cultures. Stem cells attacked by the immunoreaction died and released DAPI, which was measured by fluorometry. For determination of autoimmune T cells to stem cells, mononuclear cells were isolated from the blood of mice with stem cells transplanted by Ficoll-Paque gradient centrifugation. CD3 is a major surface marker of T lymphocytes. Therefore, CD3 positive cells were collected for assessing the cytotoxicity of T cells against stem cells in the transplanted mice. CD3-positive T lymphocytes were prepared from mononuclear cells by magnetic beads coated with anti-CD3. Stem cells were labeled with calcein (Molecular Probes). After incubation with T cells for overnight (12-16 hours), supernatants were harvested and calcein release was determined by use of a CytoFluor fluorescence plate reader.

Stem cell culture and treatment with oxysterols and cytokines. Mouse stem cells were used in this in vitro study. Two groups of proapoptotic agents were used to induce apoptosis of stem cells: oxysterols and cytokines. In group 1, stem cells were treated with 7-ketocholesterol (7-KC) and 25-OH-cholesterol (25-OH—C), two oxysterols known to exist in abundantly in atherosclerotic lesions and to induce apoptosis in cardiovascular cells. Free cholesterol was used as controls. In group 2, stem cells were incubated with a combination of tumor necrosis factor (TNF)-α and interferon (IFN)-γ, two cytokines previously shown to induce apoptosis of stem cells. In addition, to determine whether the Fas death-signaling pathway is involved in apoptosis of stem cells, stem cells were treated with recombinant Fas ligand in the presence of IFN-γ.

Clusterin treatment. In order to determine whether clusterin prevents apoptosis of stem cells, stem cells were pretreated with clusterin purified from serum or synthesized by use of recombinant technology. Stem cells were cultured in a serum-free, conditioned medium supplemented with 20-30 µg/ml clusterin for 24 hours. The preliminary data indicated no apoptosis under the culture condition with clusterin. The cells treated with clusterin were exposed to oxysterols and cytokines, respectively, as stated above. Cells were analyzed for apoptosis using the following methods after treatment. Control cells were treated under the same conditions except for no stimulation with pro-apoptotic agents.

Apoptosis induced by oxysterols. As noted above in the background discussion, free cholesterol that accumulates during the development of atherosclerosis oxidizes, producing oxysterols that have increased cytotoxicity to vascular cells. Previous in vitro studies have shown that some oxysterols such as 7-ketocholesterol (7-KC) and 25-OH-Cholesterol (25-OH—C) exerts potent apoptotic effects on stem cells. Oxysterols are considered to be major cytotoxic components of oxidized low density lipoprotein (oxLDL). It was previously unclear, however, whether apoptosis plays a role in the development of neocardiovascular tissues. In the present studies, it was investigated whether clusterin can prevent or attenuate apoptotic effects of oxLDL or oxysterols, and underlying molecular mechanisms in stem cells and their progeny. To determine the effect of clusterin on apoptosis of stem cells and macrophages induced by oxysterols in vitro, stem cells were cultured in a lipoprotein-deficient medium. At subconfluence, the cells were treated with 7-KC and 25-OH—C at 30 µg/ml each in the presence or absence of clusterin at 100 µg/ml. Thereafter, the cells were collected for the studies of apoptosis. As described above, the following assays were performed to determine the occurrence of apoptosis: analysis of cellular and nuclear morphology, DNA isolation and electrophoresis, FITC-annexin V binding assay, and immunocytochemistry for caspases and Bcl2 family proteins.

Detection of oxysterol-clusterin complexes by Eastern-Western blotting. As an apolipoprotein, clusterin contains a peptide sequence that is highly hydrophobic. To demonstrate the interactions between clusterin and oxysterols in the arteries of apoE-null and wild type mice at different ages, it was determined whether clusterin can form complexes with oxysterols using immunoprecipitation and GC-MS spectroscopy. Total proteins extracted from the aortas under various protease inhibitors were mixed with anti-clusterin antibody, and the clusterin complex was separated by affinity chromatography. The clusterin lipid content was determined by GC-MS spectroscopy as described above. To more directly visualize the formation of clusterin and oxysterol complexes, a newly developed method for assessing lipid-protein interactions in vitro was used. This technique so called Eastern-Western blotting combines thin layer chromatography (TLC) and immunoblotting and provides a sensitive methodology to detect complex formation and conformation alterations between lipids and proteins. In brief, lipids were extracted from the aortic tissue in methanol/chloroform (2:1). The lipids were separated by TLC (mobile phase: hexanes:methanol:ethyl ether, 96:15:8). Oxysterol standards were used in the same plates as controls. Lipids were visualized by exposure to iodine. After TLC separation, the lipids and oxysterol standards were transferred from the TLC plate onto a PVDF membrane using a heat-blotting device at 70-80° C. The membrane with lipids transferred were then used for Western or immunoblotting. Total aortic proteins separated by SDS-PAGE were blotted onto the membrane using a BioRad semi-dry transferor. The membrane was incubated with anti-clusterin, and developed using a peroxidase-ECL system (Amersham/Pharmacia).

Efflux of oxysterols. To analyze the role of clusterin in efflux of intracellular oxysterols, a macrophage culture system is used. Peritoneal macrophages and stem cells isolated from apoE-null mice are incubated with a serum-free medium containing acetylated LDL with $^3$H-oxysterols such as $^3$H-7-KC and $^3$H-25-OH—C. After incubation for 24 hours, the cells are incubated with different concentrations of clusterin purified by affinity chromatography. The control experiments are performed by incubating the cells with albumin at the same concentrations. After 24, 48 and 72 hours, samples of the culture medium and the treated cells are collected for oxysterol assays by liquid scintillation counting.

Effects of oxysterols on expression of clusterin. It was hypothesized that oxysterol exposure itself may actually influence expression of clusterin and thereby promote apoptosis of vascular cells in the arteries during aging. To test this hypothesis, stem cells were treated with 7-KC (30 μg/ml) and 25-OH—C (30 μg/ml), and extracted RNA and proteins from the treated and untreated cells after incubation for 24, 48 and 72 hours. Northern blotting and immunoblotting were performed for detection of clusterin mRNA and protein, respectively. To normalize sample loading and compare the clusterin levels to the "house-keeping" gene products, such as β-actin, the mRNA and protein of β-actin were also analyzed.

Apoptosis and caspase activation induced by oxysterols and CD95L (FasL). To determine whether clusterin can inhibit apoptosis of cardiovascular stem cells, DNA fragmentation, TUNEL and morphological alterations in stem cells treated with 7-ketocholesterol and CD95L in the presence or absence of clusterin were examined. Cell viability was evaluated by fluorescent microscopy with the fluorochrome dyes, acridine orange and ethidium bromide. Caspase activation was also analyzed using the following methods. (i) Analysis of endogenous substrates for caspases. In order to verify the presence of activated forms of caspases, several cellular proteins were analyzed which are known as caspase substrates, such as gelsolin and poly(ADP-ribose) polymerase (PARP). Immunoblotting can be used for determination of the caspase cleavage of the two cellular proteins. To clarify whether the caspase activation induced by CD95L is dependent on cyt-C release from mitochondria, in vitro model was used in which cytosolic cyt-C was tested for its capability of activating caspase-9. After incubation for 2 hours at 37° C., the protein samples were analyzed by immunoblotting with antibodies to caspase-3, caspase-8, and caspase-9. Addition of cyt-C lead to activation of caspase-9 and caspase-3 but not or less caspase-8, as the latter is primarily activated by a non-mitochondrial mechanism. (ii) Caspase activities. For determination of caspase activity, fluorogenic and chromogenic assays were also used for determining the caspase activity. Because the caspases have overlapping cleavage sites, these assays are not specific for individual caspases. However, the information from these assays is helpful in terms of overall evaluation of the caspase activities in the cells. Vascular cells were treated with oxysterols and harvested the cells by trypsinization. After washed in ice-cold PBS by centrifugation, the cells were homogenized with 20-30 strokes in a tight-fitting Dounce homogenizer. The homogenate was centrifuged and supernatant were used for the caspase substrate cleavage assays with the fluorogenic substrate Ac-DEVD-AFC. The reaction was incubated at 37° C. and continuous monitoring of fluorochrome release was utilized to examine the kinetics of product release and/or the kinetics of enzyme inhibition. The fluorescence was measured using an excitation wavelength of 360 nm and an emission wavelength of 475 nm. The absolute amount of fluorochrome released is determined by measuring the fluorescence of a panel of standards containing various amounts of the liberated fluorophore. As an alternative to the molecular genetic approach, it is appealing to attempt to inhibit caspase activities with specific inhibitors. In this regard, the caspase-3 inhibitor, N-(acetylaspartyl-glutamylvalinyl)-3-amino-3-formyl-propionic acid (Ac-DEVD-CHO), was added to the cultures treated with or without oxysterols. The caspase-3 activities in cleavage of its endogenous (gelsolin and PARP) and exogenous (AC-DEVD-AFC) substrates was examined by immunoblotting and fluorometry, respectively.

Figure 3:
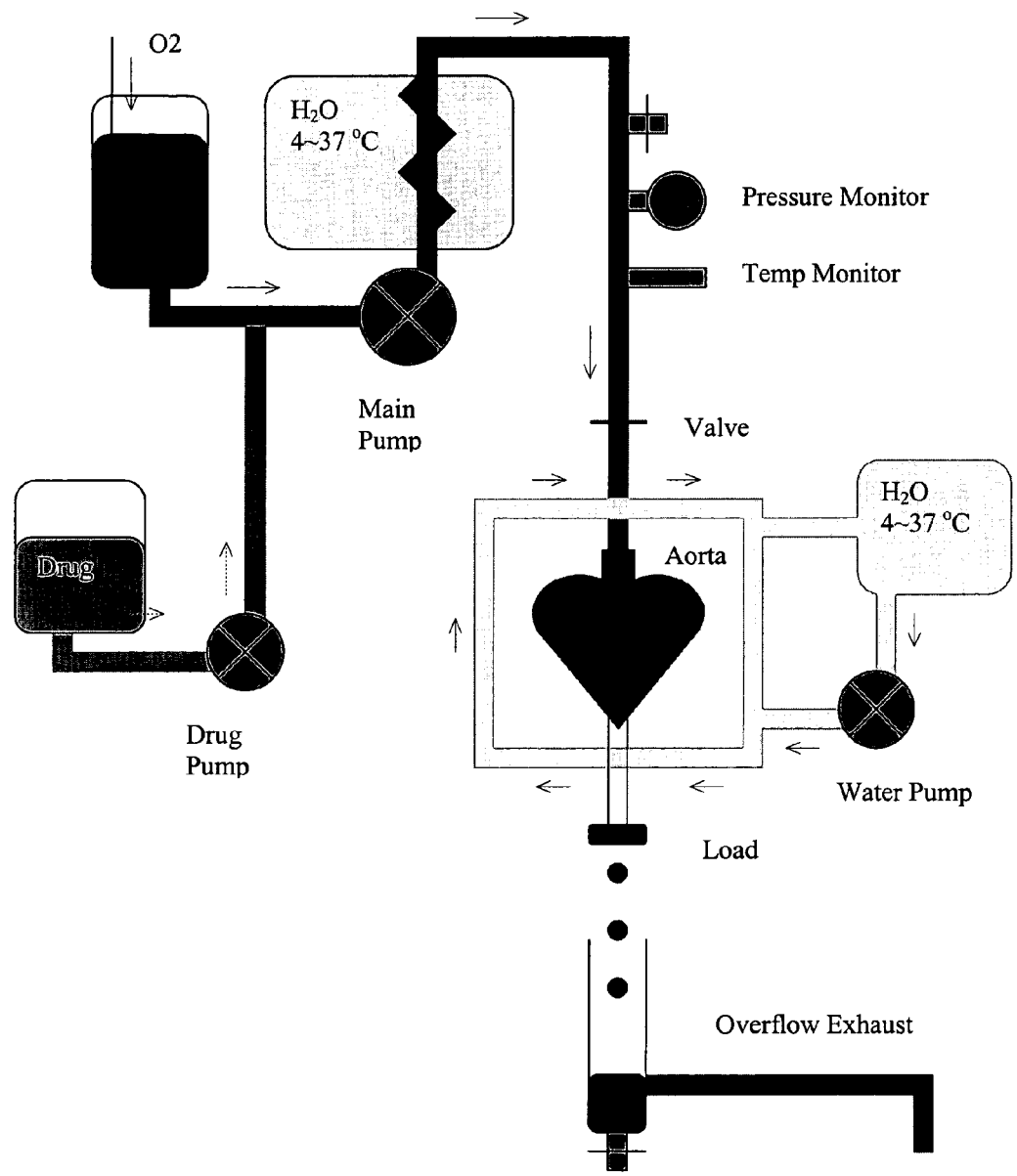
FIG. 3 is a schematic flow diagram of the Lengendorff system for ex vivo analysis of function of the hearts with or without stem cell transplantation.

Ex vivo and in vivo studies on apoE-null mice. ApoE-null mice develop hypercholesterolemia and severe atherosclerosis highly resembling the human situation. It was hypothesized that stem cells may undergo high levels of apoptosis in the apoE-null hearts than in the wild animal hearts. To test that hypothesis, in addition to the in vitro studies, two different experiments were performed. In the first experiment, a Langendorff ex vivo heart perfusion model was used to determine the oxysterol proapoptotic effects on stem cells. A schematic flow diagram of the Lengendorff system for ex vivo analysis of function of the hearts with or without stem cell transplantation is shown in FIG. 3. The contraction and electrophysiology of the hearts were recorded. Stem cells with or without oxysterols were mixed at different concentrations and then perfused the cell-oxysterol mixtures into the heart. Apoptosis of stem cells passing through the hearts was determined and compared with those stem cells which stay inside the hearts. ApoE-null and wild type animal hearts were used to examine whether there is a difference in stem cell death between apoE-null and wild type hearts. The advantage of using the Langendorff model is that the effects of hemadynamic alterations and other in vivo factors could be excluded. The second approach was in in vivo studies with apoE-null mice. Infarcts were generated in apoE-null and wild type control mice by open chest surgery as stated in Aim I. Fluorescently labeled stem cells were transplanted into the myocardium of apoE-null mice and controls. Stem cells were pretreated with or without oxyserols and injected with or without clusterin to determine whether clusterin exerted protective effects on the stem cells transplanted. The animals were closely monitored and echocardiography and EKG was conducted to determine functional changes in the hearts. The hearts were collected for the pathological studies for immunohistochmistry and morphological evaluation. In some studies, the heart was also isolated and the Lengendorff perfusion and function analysis of the isolated hearts were performed.

The hearts were perfused with Krebs-Henseleit buffer under 5% $CO_2$ and 95% $O_2$. A latex balloon was put into the left ventricle through the mitral valve and connected to a pressure transducer, a transducer amplifier, and a differentiator amplifier (Gould Instrument System, Valley View, Ohio). After 30 min of stabilization, the coronary flow of the heart was determined in triplicates by timed collection in the empty beating state. The systolic and diastolic pressures were recorded and the developed pressure will be calculated. The heart weight and body weight was measured.

Clusterin levels in blood and in the HDL fraction in clusterin transgenic mice. A clusterin transgenic mouse strain was established using a transgenic construct containing a CMV promoter, a tetracycline-regulated element, and growth hormone poly (A) sequence. To evaluate the levels of clusterin in the blood, an ELISA method was developed with monoclonal antibody against clusterin. The blood samples were collected from the mice during tail DNA sampling. Serum was prepared from the blood samples. Cholesterol levels, lipoprotein profiles and clusterin concentrations were determined respectively. In brief, 100 µl of serum diluted in PBS was incubated in a 96 well plate coated with a rabbit polyclonal antibody to clusterin. After incubation and washing in PBS, bound clusterin was detected by incubating with mouse monoclonal antibody to clusterin. Goat anti-mouse IgG conjugated with peroxidase was used as the second antibody. Cholesterol and HDL was determined in the laboratory of Department of Laboratory Medicine. The ratio of clusterin vs. HDL was calculated after normalization with the lipid content. In addition to ELISA, immunoblotting assays were performed to verify the results from ELISA. 20 µg/lane of serum proteins was loaded into 10% SDS-PAGE. After electrophoresis, protein bands were transferred to a membrane and stained with anti-clusterin. Immunoperoxidase method was used to detect clusterin bands.

Expression of clusterin protein and mRNA in the heart and other tissues. Clusterin expression in arterial tissues has been shown in previous studies. However, there has been little information as to whether there is a difference in clusterin expression between animals with and without atherosclerotic coronary disease. Therefore, in the present studies, quantitative morphological analysis of clusterin expression in the heart and aorta was conducted. Immunohistochemistry was performed using monoclonal anti-clusterin. In some cases, double staining was performed by combining TUNEL staining with anti-clusterin staining. The sections were stained by TUNEL and then subjected to immunostaining with anti-clusterin. Immunoblotting assays were conducted in order to backup the data from immunohistochemistry. Total proteins extracted from plaques were examined with anti-clusterin using the method described above. Clusterin mRNA was evaluated using real time RT-PCR. The real time RT-PCR is a very useful method which is highly sensitive and reliable. Total RNA was isolated from plaques and converted into cDNA by reverse transcription followed by amplification with Taq polymerase. A real-time PCR cycler was used to quantitatively determine the levels of clusterin mRNA.

Correlation of clusterin expression to changes in cellularity and TUNEL positivity. To determine the relationship of clusterin expression and cell accumulation, the cellularity and TUNEL positivity in the regions with higher or lower expression of clusterin were examined. Thus, double staining with a combination of anti-clusterin immunostaining and TUNEL were performed using the method described above. For evaluation of the cellularity, immunohistochemistry was performed with cell type-specific antibodies, such as anti-α-SM-actin for vascular smooth muscle cells, anti-cardiac myosin or sarcomeric actinin for cardiac myocytes, anti-CD3 for T cells, and anti-MAC3 or CD68 for macrophages. Nuclear counterstaining was carried out with the DNA-binding fluorescent dye DAPI.

Generation and characterization of GFP-tagged stem cells. Green fluorescent protein (GFP) cloned from *Aequorea victoria* absorbs blue light and emits a green fluorescence. The GFP fluorescence is stable and species-independent, and it does not require any substrates or cofactors. Hence, GFP has been extensively utilized as a living marker for transient and stable transfection analysis. In the present studies, in order to label fetal myoblasts with GFP for cell implantation, fetal cells were transfected with a plasmid containing a cDNA insert coding for GFP. After 24 hours of transfection with the GFP cDNA, the cells were examined under a fluorescent microscope. Positive cells illustrated a vivid green fluorescence in cytoplasm under a ultra-violet fluorescent microscope, indicating expression of GFP in the cells. A pilot study showed that the GFP-positive cells have morphology similar to their parent, non-transfected cells as well as to the GFP-negative cells in the same cultures. To establish a stable cell line, the stem cells with stable GFP expression were further selected by transfecting with a plasmid containing both GFP cDNA and neomycin-resistant gene. After transfection, the cells were exposed to G418 to eliminate untransfected, GFP-negative cells. Although normally GFP has no cytotoxicity to cultured cells, the possibility of this protein being able to affect differentiation of the stem cells into cardiac cells when it is overexpressed could not be ruled out. Therefore, by immunocytochemistry and immunoblotting, the expression of several proteins markers known to be present in cardiac myocytes were examined. GFP-expressing cardiac stem cells and their daughter cells displayed strong fluorescent signals for sarcomeric α-actinin and cadherins.

Transplantation of stem cells. Two approaches were used to transplant stem cells into the hearts. The first one transplanted non-transgenic stem cells into the clusterin-transgenic hearts with or without infarction. At this part of the experimentation, it was determined whether stem cells better survive and differentiate in an environment with exogenous clusterin over-expressed. In the second part of the experimentation, stem cells were isolated from fetal clusterin transgenic hearts or adult bone marrow, and were transplanted into wild type, non-transgenic hearts. This experiment was designed to determine whether endogenous expression of clusterin promotes stem cell survival and differentiation in the hearts with infarction. All the stem cells were labeled with GFP by cDNA transfection as described above.

Echocardiography. After transplantation of the stem cells, morphological and functional changes were monitored using echocardiography. 2D and M-Mode echocardiography was performed one, two, and four weeks after transplantation. The echocardiography studies were conducted actually using ultrasonography as the murine heart is small. Mice were anesthetized with ketamine and xylazine, chests shaved and a layer of acoustic coupling gel will be applied to the thorax. A dynamically focused 9-MHz annual array transducer was applied using a warmed saline bag as a standoff. All echo studies were performed using a state of the art echo machine (HP Model Sonos 5500 HP). Area fractions were determined by planimetry of diastolic and systolic volumes in parasternal short axis. The LV end-diastolic and end-systolic dimensions were measured using the M-Mode from >3 beats by two independent investigators blinded to the research animals. LVEF (left ventricular ejection fraction) was calculated as follows: LVEF=[(LVIDd)−(LVIDs)]/(LVIDd), LVIDd: end-diastolic left ventricular internal diameter; LVIDs: end-systolic left ventricular diameter.

ECG and Patch-clamp studies. Electrophysiological changes are important features of cardiac dysfunction during myocardial infarction or ischemic heart failure. To characterize the electrophysiological alterations in the infarcted heart with stem cell transplantation, two approaches were used: one is the in vivo study with electrocardiogram (ECG), and other one is the in vitro study with the patch-clamp technique to measure ion channel functions. ECG was recorded and analyzed for changes in electrophysiology such as QRS waves and ST segment. For patch-clamp studies, myocytes were isolated from the hearts with or without stem cells transplanted. Since stem cell-derived myocytes showed green fluorescence, the green cells were selectively analyzed under a fluorescence microscope. For patch clamp recording only spontaneously beating, single cardiomyocytes were selected, using the whole-cell configuration. Myocytes were held in the voltage-clamp mode using an Axopatch 200-A amplifer. For $I_f$ measurements, cardiomyocytes were clamped at a holding potential of −35 mV or 200 ms to obtain inactivation of sodium currents and hyperpolarizing voltage steps. The patterns of hyperpolarization helped determine which type of cardiac cells the stem cell-derived myocytes belong to. The amplitude of $I_f$ was measured as the difference between the instantaneous current at the beginning of the voltage step.

Receptor expression. Cardiomyocytes can express several important surface receptors which are critical for regulation of myocyte contraction, in particular adrenergic and muscarinic receptors. To determine expression of those receptors, RT-PCR and immunoblotting were performed. Total RNA and proteins was isolated from the hearts. Specific PCR primers were used for determination of α1A, α1B, α1D, β1, β2, M1 and M2 receptors. Several house-keeping genes were also analyzed including β-actin and GAPDH. For immunoblotting, the proteins were fractionated in a 10% SDS-PAGE, and then transferred the protein bands onto a PVDF membrane. Monoclonal or polyclonal antibodies against these receptors were used to probe the protein bands on the membrane. Immunostains were developed using a chemiluminescence kit.

Histology and immunocytochemistry. To determine whether transgenic overexpression of clusterin helps integration of more stem cell-derived myocytes into the host myocardium, immunohistochemistry with anti-myocyte specific antibodies was performed. Mice were sacrificed 4-8 weeks after surgery for morphological analysis. Full core biopsies of the fetal cell injected areas were taken and preserved in 3% gluteraldehyde for electron microscopy. The hearts were rinsed thoroughly in ice cold saline and perfused with 2,3,5-Triphenyl-Tetrazolium Chloride (TTC) and Evan's blue dye to determine the area at risk and infarcted area. The heart was then sliced across the long axis and each slice was photographed on each side for infarct size. The sliced heart was then placed in 10% buffered formalin for histological evaluation. Control studies were done in the same manner except that saline rather than fetal cells were injected. Histological evaluation of the infarcted myocardium with and without cell implantation was conducted by H&E staining and electron microscopy. Expression of cardiovascular cell markers was identified in both cultured myoblasts on 8-chamber slides and in sections of the myocardium with antibodies (Sigma, St. Louis, Mo.), against sarcomere α-actinin, pan-cadherin, anti-desmin, and α-smooth muscle actin (SM-α-actin). In order to assess actin cytoskeleton, the sections were also stained with rhodamine-phalloidine (Sigma, St. Louis, Mo.). After incubating with primary antibodies and rinsed in PBS, the slides were stained with biotylated antimouse or anti-rabbit IgG (Sigma, St. Louis, Mo.), followed by incubation with streptavidin linked with TRITC or FITC. The slides were mounted in the Vectashield mounting medium with 4',6 diamidino-2-phenylindole (DAPI) (Vector, Burlingame, Calif.), and examined under an Olympus fluorescence microscope.

EXAMPLE 1

Establishment of a Murine Infarct Model

Figure 4A:
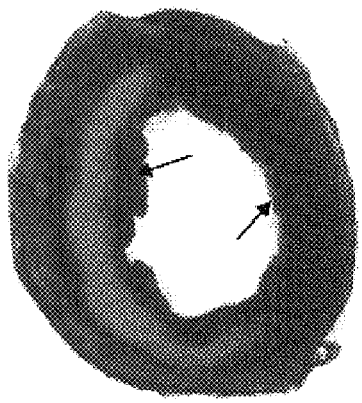
FIGS. 4A-B are representative photomicrographs of tissue sections showing myocardial infarct (FIG. 4A) and apoptotic cell death (FIG. 4B) in the murine heart.
Figure 4B:
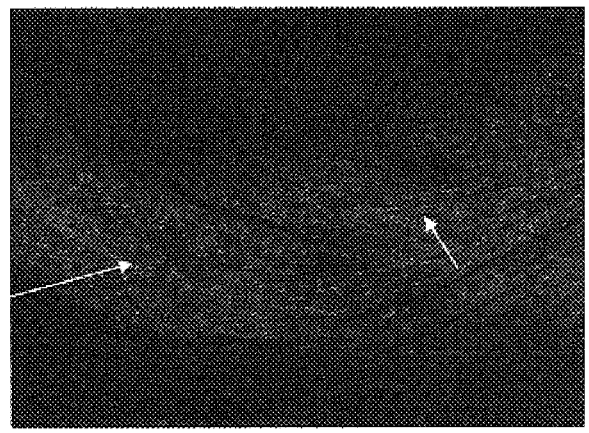

In order to test the apoptosis and development of stem cells in the heart with ischemic injury, a murine model was established for cell transplantation. Open chest surgery was performed on C57BL/6J mice under anesthesia. After coronary ligation for one hour, the hearts were reperfused for 30 min and then sacrificed 2 weeks later. The hearts were perfused-fixed in formalin. Cell death by apoptosis was determined by in situ labeling (TUNEL) of DNA fragments. Typical infarcts were observed in the myocardium injured by ischemia-reperfusion (FIG. 4A-B). Many TUNEL positive nuclei exist in the lesions. FIG. 4A, left ventricular section, TTC/blue dye staining showing an infarct in the heart (indicated by arrows); and FIG. 4B, numerous TUNEL positive (green fluorescent) nuclei in infarcted and surrounding areas, indicated by white arrows.

EXAMPLE 2

Apoptosis of Cardiac Stem Cells and Clusterin Treatment

Figure 5A:
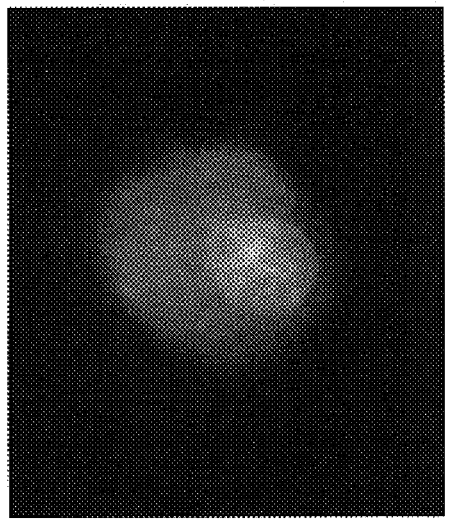
FIGS. 5A-B are representative photomicrograph images of murine cardiac stem cells cultured in the presence (FIG. 5A) or absence (FIG. 5B) of clusterin.
Figure 5B:
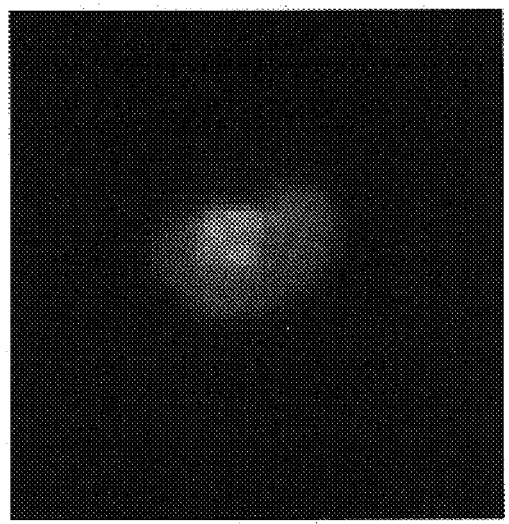

The effect of clusterin on apoptosis of cardiac stem cells induced by serum starvation was tested. as described above in the General Methods and Materials. Cardiac stem cells were prepared from the newborn murine heart by gradient centrifugation. In the presence of clusterin-containing DMEM medium (FIG. 5A), the cardiac stem cells showed no sign of apoptosis while many cells died without clusterin. The dead cells exhibited a morphology characteristic of apoptosis including cell shrinkage, chromatin condensation, and nuclear fragmentation (FIG. 5B). In FIGS. 5A,B, images of murine cardiac stem cells in the presence (FIG. 5A) or absence (FIG. 5B) of clusterin. Cells were stained with acridine orange and ethidium bromide, and images were taken under an Olympus fluorescence microscope with ×40 objective.

EXAMPLE 3

GFP Expression by cDNA Transfection in Fetal Cardiac Myoblasts

A cDNA transfection method was established by which cardiac myoblasts or stem cells can be labeled with GFP. A plasmid was constructed with a neomycin-resistant gene. The transfected cells were selected using G418. GFP labeled cells can differentiate into mature myocytes in the same way as their parent cells. FIGS. 6A,B are representative images of GFP-transfected fetal cardiac myoblasts, illustrating GFP cDNA transfection leading to expression of the green fluorescent protein (GFP) in fetal cardiac myoblasts. Fetal cardiac myoblasts cultured in DMEM medium were transfected with a plasmid containing an insert coding for GFP. FIG. 6A is a phase-contrast image; and FIG. 6B is a fluorescent image showing GFP positive cells 48 hours after transfection

EXAMPLE 4

Figure 7A:
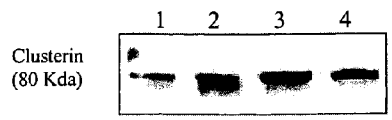
FIGS. 7A-C are an immunoblot and photomicrographs showing that intracellular expression of clusterin inhibits apoptosis in KG-293 cells.
Figure 7B:
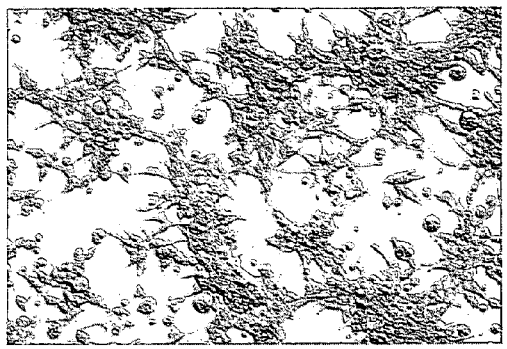
Figure 7C:
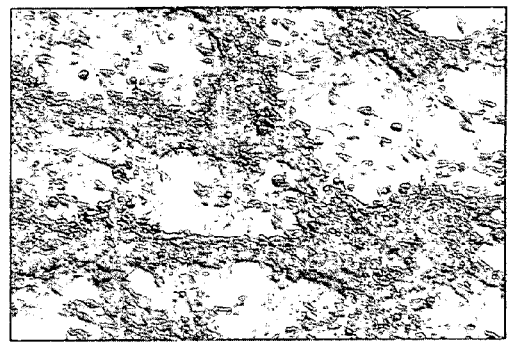

Transfection of Embryonic Cells with Clusterin cDNA and Inhibition of Apoptosis by Clusterin A plasmid pKS7 that contains a truncated clusterin cDNA with deletion of the transmembrane domain and a neomycin-resistant gene was constructed. The truncated clusterin gene was under regulation by a CMV promoter with tetracycline-responding elements. Stable transfection of the human embryonic kidney cell line T-293 with pKS7 generates a stable cell line (KG-293) with clusterin overexpressed. As shown by Western blot, under stimulation with tetracycline (1 µg/ml) for 24 hours, KG-293 cells but not their precursors, T-293 cells, produced an intracellular form of clusterin at much higher levels (FIG. 7A). Treatment with tumor necrosis factor-α (TNF-α) at 10 ng/ml for 24 and 48 hours markedly induced apoptosis in the control KG-293 cells that were not exposed to tetracycline. The pro-apoptotic effect of TNF-α was significantly attenuated in KG-293 cells with intracellular overexpression of clusterin (FIGS. 7B and 7C). KG-293 cells overexpressing the intracellular form of clusterin also underwent dramatic alterations in morphology and proliferation. The cells tended to aggregate and showed proliferating figures. Thus, intracellular overexpression of clusterin in the human embryonic cells markedly increases their resistance to apoptosis induced by TNF-α, indicating that the cytoplasmic form of clusterin may function as an intracellular regulator of apoptosis. Thus, overexpression of clusterin by cNDA transfection inhibits apoptosis induced by TNF-α in 293 embryonic cells. FIGS. 7A-C show that intracellular expression of clusterin inhibits apoptosis in KG-293 cells. FIG. 7A: immunoblotting showing clusterin expression in tetracycline-uninduced (lanes 1, 2) and -induced (lanes 3, 4) cells. FIG. 7B: apoptosis in non-induced, clusterin-low cells; and FIG. 7C, induced, clusterin-high cells.

EXAMPLE 5

Establishment of Transgenic Mice with Overexpression of Clusterin

Figure 8:
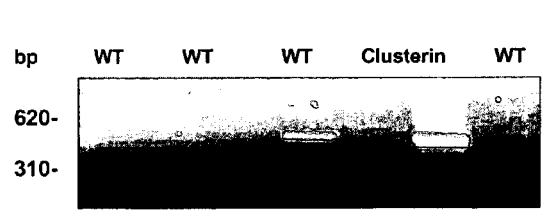
FIG. 8 is a photograph of an agarose gel after electrophoresis of PCR products of clusterin transgenic mice genomic DNA and UV visualization.
Figure 9:
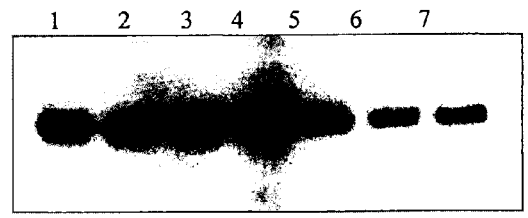
FIG. 9 is an immunoblot showing clusterin expression in clusterin transgenic (TG) and wild type mice. Lanes 1-5: transgenic. Lanes 6-7: wild type.

Several transgenic mice expressing high levels of clusterin were established. Mouse clusterin full-length cDNA was cloned from RNA using PCR-aided cDNA cloning strategy. A 1.5 Kb clusterin cDNA fragment was inserted into the pUni/V5-His TOPO vector (Invitrogen), and the insert was verified by sequencing. The transgenic construct was composed of a CMV promoter and PGH poly (A) sequence in addition to the clusterin insert. The transgene was delivered by microinjection to C57BL mice. Genotyping by PCR clearly showed the establishment of clusterin transgenic mice (FIG. 8). In FIG. 8, the results of PCR genotyping of clusterin transgene in C57BL/6J mice are shown. Genomic DNA isolated from mouse tails was amplified by PCR with a set of primers specific for clusterin transgene. After 35 cycles, PCR products were analyzed by agarose gel electrophoresis and visualized under UV light. Two transgenic mice were clearly identified. As shown in FIG. 9, Western blot with anti-clusterin antibody further confirmed that the transgenic mice had 2-3 fold-increased clusterin at the protein levels. In FIG. 9, the results of immunoblotting for clusterin in clusterin transgenic (TG) and wild type mice are shown. 30 µg/lane serum proteins were loaded into SDS-PAGE, and after electrophoresis transferred onto PVDF membrane, and developed with an ECL kit. Lanes 1-5, transgenic; and lanes 6-7, wild type.

EXAMPLE 6

Clusterin Selectively Binds to Oxysterols

As a component of HDL, clusterin helps transport cholesterol crossing the cellular membrane. In atherosclerotic lesions, cholesterol-derived oxysterols accumulate and exert apoptotic effects on vascular cells. Usually, the cytotoxicity of oxysterols including 7-ketocholesterol is much greater than that of free cholesterol. By dot blotting, it was observed that clusterin bound to 7-ketocholesterol at much higher intensities than free cholesterol when these lipids were coated onto the filter (FIG. 10). In FIG. 10, dot blotting shows clusterin binding to free cholesterol and 7-ketocholesterol in clusterin transgenic (TG) and wild type (WT) mice. Free cholesterol and 7-ketocholesterol dissolved in ethanol were loaded to a filter in a 96-well dot blotting device. 10 µg/well proteins from three TG and WT serum samples were incubated in the wells for 30 min at room temperate. After washing with PBS, the filter was incubated with anti-clusterin antibody (1:200), and then anti-goat IgG conjugated with peroxidase. The dot blotting was developed using an ECL kit. Furthermore, an increased binding activity to the oxysterol in the serum from clusterin transgenic mice, compared to these in wild type mouse serum (FIG. 10), was detected. Thus, clusterin appears to have a higher affinity to some oxidized cholesterol derivatives.

EXAMPLE 7

Clusterin-Induced Expression of Genes Involved in Detoxification

Figure 11:
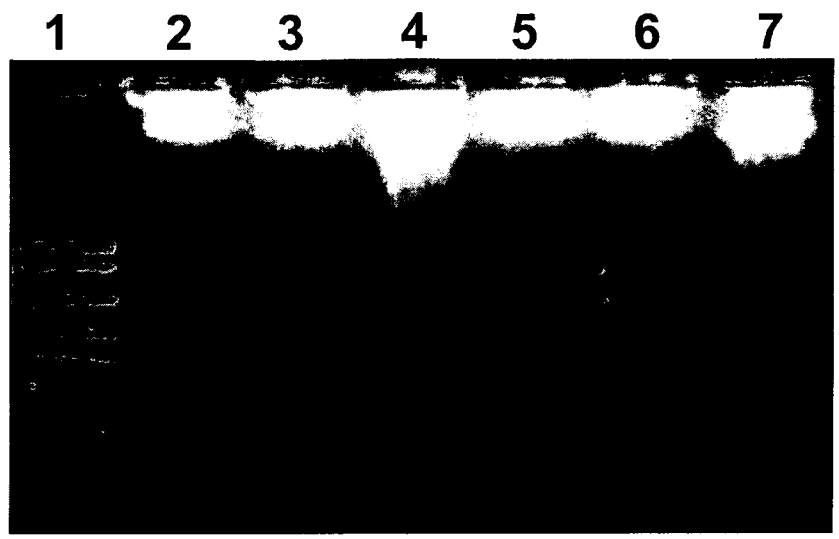
FIG. 11 is an ethedium bromide-stained agarose gel loaded with DNA samples extracted from clusterin-transfected or non-transfected vascular smooth muscle cells.

Information about the synthesis and expression of several clusterin associated or regulated proteins were also obtained. These proteins include, but are not limited to, caspases, high density lipoproteins, apolipoprotein-AI, paraoxonase, and aldehyde dehydrogenase. Caspases are a group of aspartate-specific cysteinyl proteases that function as effectors in apoptosis.[9, 10] Clusterin functions as a stress responding protein that interacts with intracellular caspases and regulate the enzyme activation and substrate cleavage. Thus far, more than 14 members of the caspase family have been identified in non-cardiovascular tissues, particularly in the immune and nervous systems. All members of the caspase family show a similar substrate cleavage at an aspartate residue, and they are synthesized as proenzymes. This protease family participates in downstream events of death signaling by the members of TNF receptor family (e.g., CD95 or Fas and TNF receptor-1) which share a related intracellular "death domain" of about 70 amino acid residues. Activation of caspase-8 by CD95 or Fas death signaling may have two effects. First, it may directly trigger caspase-3 activation, leading to mitochondrial-independent apoptosis; secondly, activated caspase-8 may promote cytochrome-C (Cyt-C) release from mitochondria by cleavage of Bid, a bcl2 family member that is a substrate for caspase-8. After released from mitochondria, Cyt-C forms a complex with Apaf-1 and caspase-9, leading to caspase-9 activation. The Bcl-2 protein family represents another group of cellular proteins that regulate apoptosis in mammalian cells.[11] The mitochondrial membrane contains abundant Bcl-2. The Bcl-2 family has more than 15 members. Based upon differences in regulation of apoptosis, members of this family fall into two subgroups. Each of them contains five or more function- and structure-related proteins. The first group includes the anti-apoptotic proteins such as Bcl-2, Bid, Bcl-X, Mcl-1, Bcl-w and A1; members of the second group promote apoptosis and include Bax, Bak, Bad, Bik, Hrk, Bid and Bcl-xs. The mechanism by which Bcl-2 inhibits apoptosis remains incompletely clarified. Bcl-2 may exert an antioxidant effect on stressed cells, prevent release of mitochondrial Cyt-C, and bind to and inactivate pro-apoptotic molecules such as Bax and Bak. Rapidly accumulating evidence indicates the pivotal role of mitochondria in apoptosis. Mitochondria can regulate apoptosis in at least three ways: 1) inhibition of mitochondrial respiration due to production of large amounts of NO in cytokine-stimulated vascular cells; 2) production of cytotoxic reactive oxygen species or change of cellular reduction-oxidation (redox) potential; and 3) release of pro-apoptotic molecules including cytochrome-c and apoptosis inducing factor (AIF). Many Bcl-2 family proteins reside in the mitochondrial outer membrane where they form a pore structure that resembles surprisingly some bacterial toxins enhancing proton extrusion. The release of cytochrome-c depends on the mitochondrial inner transmembrane potential. When apoptotic stimuli attenuate Bcl-2 function, a rapid drop or collapse of transmembrane potential may occur, causing rapid release of cytochrome-c and other pro-apoptotic proteins. Cytosolic cytochrome-c then forms, together with Apaf-1 and caspase-9, an "apoptosome" which orchestrates activation of other caspases and distal effectors of apoptosis. Exposure to oxidized low density lipoprotein (oxLDL) or its associated oxysterols, such as 7-ketocholesterol, can trigger apoptosis of vascular smooth muscle cells, evidenced by internucleosomal DNA fragmentation due the apoptosomal activation (FIG. 11). However, overexpression of clusterin by cDNA transfection markedly reduces the DNA fragmentation and apoptosis in the vascular cells induced by the oxysterol (FIG. 11). These results indicate that clusterin exerts protective effect on oxysterol-induced vascular cell apoptosis.

EXAMPLE 8

Clusterin Regulated Enzyme Expression

Aldehyde dehydrogenase expression and vitamin A metabolism were investigated to determine whether clusterin exerts its protective effect through upregulation of genes involved in cellular detoxification. Aldehyde dehydrogenases (ALDHs) are a group of intracellular enzymes that mediate NAD-coupled oxidation of aldehydes to carboxylic acids. ALDH is probably most widely known for its role in clearance of acetaldehyde from beverage alcohol by conversion to acetic acid. This enzymes is also involved in retinol metabolism and mediates vitamin A function. Members of the ALDH family are diversed; some have broad substrate specificities (ALDH1 and ALDH2) and other ALDHs are tailored to specific reactions of intermediary metabolism (e.g., methyl malonic semialdehyde dehydrogenase in branched-chain amino acid metabolism). ALDH1 is primarily found in the liver and in adult stem cells including hematopoietic stem cells. For instance, no physiological role is known for ALDH2, yet a single amino acid substitution (E487K) is sufficient to abolish activity, even in heterozygotes, with no apparent adverse effect except that it provides the underlying cause of severe aversion to beverage alcohol in about 50% of Asian individuals. Interestingly, ALDH2 has recently also been identified as responsible for the initial step in the pathway leading to nitric oxide from nitroglycerin, as used in treating angina. (ALDH2 converts nitroglycerin to 1,2 glyceryldinitrate and nitrite.)

Figure 13:
FIG. 13 is an immunoblot showing induction of aldehyde dehydrogenase-1 (ALDH-1) in murine vascular smooth muscle cells by treatment with recombinant human clusterin (apoJ) at different concentrations (lane 1, 0 µg/ml; lane 2, 5 µg/ml; lane 3, 25 µg/ml; lane 4, 50 µg/ml).
Figure 14:
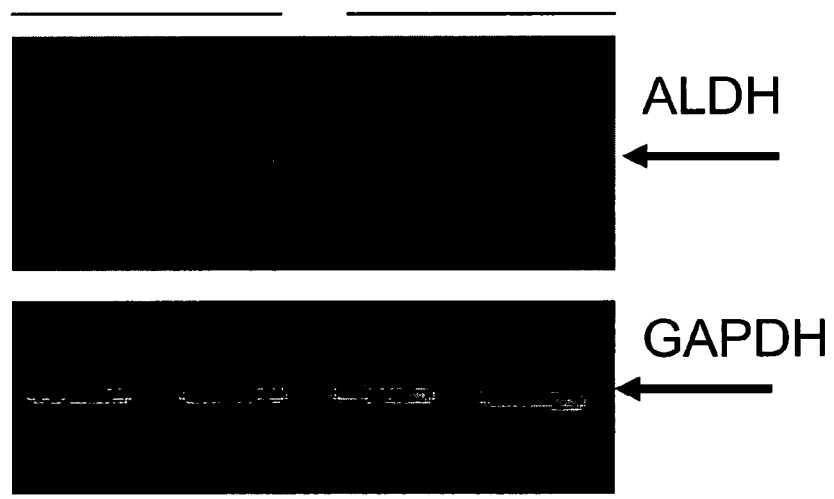
FIG. 14 is a post-electrophoretic, ethedium bromide-stained agarose gel with the products of RT-PCR for ALDH-1 mRNA (upper panel) and Glyceraldehyde 3-Phosphate Dehydrogenase (GAPDH) (lower panel) in clusterin (apoJ) transgenic and wild type mice.

Other ALDHs are tailored to specific reactions of intermediary metabolism (e.g., methyl malonic semialdehyde dehydrogenase in branched-chain amino acid metabolism). Aldehyde dehydrogenases (ALDHs) mediate NAD-coupled oxidation of aldehydes to carboxylic acids. ALDH is probably most widely known for its role in clearance of acetaldehyde, from beverage alcohol, by conversion to acetic acid. However, the ALDH family is a highly divergent one. A variety different forms with clear evolutionary relationships are known in humans. Some have broad substrate specificities (ALDH1 and ALDH2) and are primarily found in the liver. For instance, no physiological role is known for ALDH2, yet a single amino acid substitution (E487K) is sufficient to abolish activity, even in heterozygotes, with no apparent adverse effect except that it provides the underlying cause of severe aversion to beverage alcohol in ca. 50% of Asian individuals. Interestingly, ALDH2 has recently also been identified as responsible for the initial step in the pathway leading to nitric oxide from nitroglycerin, as used in treating angina. (ALDH2 converts nitroglycerin to 1,2 glyceryldinitrate and nitrite.) In order to determine whether clusterin can induce expression of ALDH genes in vascular tissue cells, recombinant human clusterin was used to treat smooth muscle cells. The treatment with purified or recombinant clusterin significantly induced expression of ALDH in smooth muscle cells in a concentration-dependent fashion (FIG. 13). Further study on expression of ALDH-1 mRNA by the reverse transcription-polymerase chain reaction (RT-PCR) demonstrated much greater expression of ALDH-1 mRNA in transgenic mice with overexpression of clusterin (FIG. 14, upper panel) when compared to those of non-transgenic or wild type mice (FIG. 14, lower panel). Thus, clusterin functions as an inducer or activator of the ALDH detoxification pathway.

The foregoing examples are offered by way of illustration, and not by way of limitation. Those skilled in the art will recognize that variations of the invention embodied in the examples can be made, especially in light of the teachings of the various references cited herein, the disclosures of which are hereby incorporated herein by reference.

REFERENCES CITED

1. Wang, J. S., D. Shum-Tim, E. Chedrawy, and R. C. Chiu, The coronary delivery of marrow stromal cells for myocardial regeneration: pathophysiologic and therapeutic implications. *J Thorac Cardiovasc Surg*, 2001. 122(4): p. 699-705.
2. Marelli, D., F. Ma, and R. C. Chiu, Satellite cell implantation for neomyocardial regeneration. *Transplant Proc*, 1992. 24(6): p. 2995.
3. Marelli, D., C. Desrosiers, M. el-Alfy, R. L. Kao, and R. C. Chiu, Cell transplantation for myocardial repair: an experimental approach. *Cell Transplant*, 1992. 1(6): p. 383-390.
4. Wang, J. S., D. Shum-Tim, J. Galipeau, E. Chedrawy, N. Eliopoulos, and R. C. Chiu, Marrow stromal cells for cellular cardiomyoplasty: feasibility and potential clinical advantages. *J Thorac Cardiovasc Surg*, 2000. 120(5): p. 999-1005.
5. Zibaitis, A., D. Greentree, F. Ma, D. Marelli, M. Duong, and R. C. Chiu, Myocardial regeneration with satellite cell implantation. *Transplant Proc*, 1994. 26(6): p. 3294.
6. Van Meter, C. H., Jr., W. C. Claycomb, J. B. Delcarpio, D. M. Smith, H. deGruiter, F. Smart, and J. L. Ochsner, Myoblast transplantation in the porcine model: a potential technique for myocardial repair. *J Thorac Cardiovasc Surg*, 1995. 110(5): p. 1442-1448.

7. Watanabe, E., D. M. Smith, Jr., J. B. Delcarpio, J. Sun, F. W. Smart, C. H. Van Meter, Jr., and W. C. Claycomb, Cardiomyocyte transplantation in a porcine myocardial infarction model. *Cell Transplant*, 1998. 7(3): p. 239-246.
8. Geng, Y. J., Y. Ishikawa, D. E. Vatner, T. E. Wagner, S. P. Bishop, S. F. Vatner, and C. J. Homcy, Apoptosis of cardiac myocytes in Gsalpha transgenic mice. *Circ Res*, 1999. 84(1): p. 34-42.
9. Green, D. R. and J. C. Reed, Mitochondria and apoptosis. *Science*, 1998. 281(5381): p. 1309-1312.
10. Thornberry, N. A. and Y. Lazebnik, Caspases: enemies within. *Science*, 1998. 281(5381): p. 1312-1316.
11. Adams, J. M. and S. Cory, The Bcl-2 protein family: arbiters of cell survival. *Science*, 1998. 281(5381): p. 1322-1326.
12. Wilson, M. R. and S. B. Easterbrook-Smith, Clusterin is a secreted mammalian chaperone. *Trends Biochem Sci*, 2000. 25(3): p. 95-98.
13. Jordan-Starck, T. C., S. D. Lund, D. P. Witte, B. J. Aronow, C. A. Ley, W. D. Stuart, D. K. Swertfeger, L. R. Clayton, S. F. Sells, B. Paigen, and et al., Mouse apolipoprotein J: characterization of a gene implicated in atherosclerosis. *J Lipid Res*, 1994.35(2): p. 194-210.
14. Jenne, D. E. and J. Tschopp, Clusterin: the intriguing guises of a widely expressed glycoprotein. *Trends Biochem Sci*, 1992. 17(4): p. 154-159.
15. Koch-Brandt, C. and C. Morgans, Clusterin: a role in cell survival in the face of apoptosis? *Prog Mol Subcell Biol*, 1996. 16: p. 130-149.
16. Silkensen, J. R., G. B. Schwochau, and M. E. Rosenberg, The role of clusterin in tissue injury. *Biochem Cell Biol*, 1994. 72(11-12): p. 483-488.
17. Rosenberg, M. E. and J. Silkensen, Clusterin: physiologic and pathophysiologic considerations. *Int J Biochem Cell Biol*, 1995. 27(7): p. 633-645.
18. Vakeva, A., P. Laurila, and S. Meri, Co-deposition of clusterin with the complement membrane attack complex in myocardial infarction. *Immunology*, 1993. 80(2): p. 177-182.
19. Silkensen, J. R., A. T. Hirsch, M. M. Lunzer, D. Chmielewski, J. C. Manivel, M. R. Muellerleile, and M. E. Rosenberg, Temporal induction of clusterin in the peri-infarct zone after experimental myocardial infarction in the rat. *J Lab Clin Med*, 1998. 131(1): p. 28-35.
20. Swertfeger, D. K., D. P. Witte, W. D. Stuart, H. A. Rockman, and J. A. Harmony, Apolipoprotein J/clusterin induction in myocarditis: A localized response gene to myocardial injury. *Am J Pathol*, 1996. 148(6): p. 1971-1983.
21. Harding, M. A., L. J. Chadwick, V. H. Gattone, 2nd, and J. P. Calvet, The SGP-2 gene is developmentally regulated in the mouse kidney and abnormally expressed in collecting duct cysts in polycystic kidney disease. *Dev Biol*, 1991. 146(2): p. 483-490.
22. Little, S. A. and P. E. Mirkes, Clusterin expression during programmed and teratogen-induced cell death in the postimplantation rat embryo. *Teratology*, 1995. 52(1): p. 41-54.
23. O'Bryan, M. K., S. S. Cheema, P. F. Bartlett, B. F. Murphy, and M. J. Pearse, Clusterin levels increase during neuronal development. *J Neurobiol*, 1993. 24(4): p. 421-432.
24. Choi-Miura, N. H. and T. Oda, Relationship between multifunctional protein "clusterin" and Alzheimer disease. *Neurobiol Aging*, 1996. 17(5): p. 717-722.
25. Mackness, B., Hun, R., Durrington, P. N., Mackness, M. I. Increased immunolocalization of paraoxonase, clusterin, and apolipoprotein A-I in the human artery wall with the progression of atherosclerosis. *Arterioscler Thromb Vasc Biol.* 1997 July; 17(7): 1233-8.

What is claimed is:

1. A method of inhibiting apoptosis in mammalian cells, comprising:
    ex-vivo, transfecting an isolated population of autologous or allogenic bone marrow stromal cells with a nucleic acid encoding clusterin protein, or encoding a truncated clusterin protein lacking the transmembrane domain, operably linked to a promoter and capable of being expressed in the resulting transfected stromal cells, wherein the stromal cells comprise bone marrow stem cells;
    in vivo, transplanting the transfected stromal cells into cardiac tissue of a mammal by direct delivery of the cells to a cardiac site where expression of clusterin is desired; and
    expressing said clusterin encoded by said nucleic acid in an amount sufficient to inhibit apoptosis in said transfected cells and/or adjacent cells.
2. The method of claim 1 wherein said cardiac tissue is in a mammal with atherosclerosis.
3. The method of claim 1 wherein said stromal cells comprising stem cells are allogenic.
4. The method of claim 1 wherein, some of said bone marrow stem cells are uncommitted and are capable of differentiating into cardiac myocytes phenotype or cardiac cells.
5. The method of claim 1 wherein said cardiac tissue of said mammal is subject to inflammatory or oxidative injury or stress.
6. The method of claim 1 wherein said step of expressing said clusterin protein encoded by said nucleic acid provides an amount of clusterin sufficient to induce an aldehyde dehydrogenase enzyme that acts as a detoxification agent for oxidized lipoproteins and oxysterols.
7. The method of claim 1 wherein said cardiac site comprises an atherosclerotic lesion.
8. The method of claim 7 wherein said atherosclerotic lesion comprises an unstable plaque.
9. The method of claim 1, wherein said mammalian tissue is exposed to at least one inflammatory agent selected from the group consisting of oxidized low density lipoprotein (ox-LDL), oxysterols, cytokines and Fas ligand.
10. The method of claim 1, wherein said inhibition of apoptosis promotes survival of said transplanted transfected stromal cells that express clusterin or said truncated clusterin protein lacking the transmembrane domain.
11. The method of claim 1, wherein said step of expressing said nucleic acid in said transfected stromal cells comprises overexpressing clusterin or said truncated clustrin.
12. The method of claim 11, wherein said overexpressing of said clusterin or truncated clusterin causes sufficient inhibition of apoptosis to deter apoptotic cell death of said transplanted stromal cells comprising stem cells.
13. The method of claim 1 wherein some of the bone marrow stem cells are uncommitted and capable of differentiating into a cardiac myocyte phenotype or cardiac cells.
14. The method of claim 1 wherein said cardiac tissue is in a mammal with heart failure.
15. A method of inhibiting apoptosis in mammalian cells, comprising:
    in vivo, transplanting an isolated population of transfected autologous or allogenic bone marrow stromal cells into cardiac tissue of a mammal by direct delivery of the cells to a cardiac site where expression of clusterin is desired, wherein said cardiac site comprises an atherosclerotic lesion or an area that is at risk of forming an atherosclerotic lesion, wherein said stromal cells comprise bone marrow stem cells, and wherein said transfected cells contain a nucleic acid encoding clusterin protein, or encoding a truncated clusterin protein lacking the transmembrane domain, operably linked to a promoter and capable of being expressed in the transfected cells; and expressing said clusterin protein encoded by said nucleic acid in an amount sufficient to inhibit apoptosis in said transfected cells and/or adjacent cells.

16. The method of claim 15 wherein said atherosclerotic lesion comprises an aneurism.

17. The method of claim 16 wherein said atherosclerotic lesion comprises an unstable plaque.

18. The method of claim 16 wherein said cardiac site is subjected to inflammatory stress.

19. The method of claim 7 wherein said atherosclerotic lesion comprises an aneurism.

\* \* \* \* \*